(12) United States Patent
Kang et al.

(10) Patent No.: US 9,723,990 B2
(45) Date of Patent: *Aug. 8, 2017

(54) TRANSMITTED LIGHT DETECTION TYPE MEASUREMENT APPARATUS FOR SKIN AUTOFLUORESCENCE

(71) Applicant: KOREA ELECTROTECHNOLOGY RESEARCH INSTITUTE, Changwon-si, Gyeongsangnam-do (KR)

(72) Inventors: Uk Kang, Seoul (KR); Garry V Papayan, St. Petersburg (RU); Il Hyung Shin, Seoul (KR); Dae Sic Lee, Seoul (KR); Soo Jin Bae, Seoul (KR); Guang Hoon Kim, Busan (KR)

(73) Assignee: KOREA ELECTRO TECHNOLOGY RESEARCH INSTITUTE, Changwon-si (KR)

( * ) Notice: Subject to any disclaimer, the term of this patent is extended or adjusted under 35 U.S.C. 154(b) by 237 days.

This patent is subject to a terminal disclaimer.

(21) Appl. No.: 13/927,712

(22) Filed: Jun. 26, 2013

(65) Prior Publication Data
US 2014/0163387 A1   Jun. 12, 2014

Related U.S. Application Data

(63) Continuation-in-part of application No. 13/845,974, filed on Mar. 18, 2013.

(30) Foreign Application Priority Data

Mar. 21, 2012 (KR) .................. 10-2012-0028724
Jul. 9, 2012 (KR) .................. 10-2012-0074251

(51) Int. Cl.
*A61B 5/05* (2006.01)
*A61B 5/00* (2006.01)

(52) U.S. Cl.
CPC .......... *A61B 5/0071* (2013.01); *A61B 5/7225* (2013.01)

(58) Field of Classification Search
None
See application file for complete search history.

(56) References Cited

U.S. PATENT DOCUMENTS 5,327,413 A * 7/1994 Fritz .................. 369/112.19
5,448,992 A   9/1995 Kupershmidt
(Continued)

FOREIGN PATENT DOCUMENTS

CN   1882278 A   12/2006
CN   100998499 A   7/2007
(Continued)

OTHER PUBLICATIONS

United Kingdom Office Action for application No. 1305226.1 dated Sep. 30, 2013.
(Continued)

*Primary Examiner* — James Kish
(74) *Attorney, Agent, or Firm* — Patent Office of Dr. Chung Park

(57) ABSTRACT

The present invention provides a transmitted light detection type measurement apparatus for skin fluorescence, which is configured to perform light irradiation and light detection on a reference sample and a measurement target. The apparatus includes a first light source, a second light source, a first optical detector and a second optical detector, a light source switching controller, and an operator.

52 Claims, 9 Drawing Sheets

(56) References Cited

U.S. PATENT DOCUMENTS

| | | | |
|---|---|---|---|
| 5,572,996 A | | 11/1996 | Doiron et al. |
| 5,676,140 A | | 10/1997 | Ukawa et al. |
| 7,660,616 B1 | * | 2/2010 | Poore .......................... 600/341 |
| 2002/0193672 A1 | | 12/2002 | Walsh et al. |
| 2004/0186363 A1 | | 9/2004 | Smit et al. |
| 2004/0233423 A1 | * | 11/2004 | Nakayama et al. .......... 356/246 |
| 2008/0097174 A1 | * | 4/2008 | Maynard et al. ............. 600/316 |
| 2008/0103373 A1 | * | 5/2008 | Matter et al. ................. 600/306 |
| 2008/0179541 A1 | * | 7/2008 | LeBoeuf et al. ........... 250/459.1 |
| 2012/0062723 A1 | * | 3/2012 | Ghosh et al. .................. 348/79 |

FOREIGN PATENT DOCUMENTS

| | | |
|---|---|---|
| CN | 101716069 A | 6/2010 |
| JP | 48-31988 A | 4/1973 |
| JP | 08-063048 A | 3/1996 |
| JP | 08-196526 A | 8/1996 |
| JP | 08-196526 A1 | 8/1996 |
| JP | 2004-290234 A | 10/2004 |
| JP | 2009-047540 A | 3/2009 |
| KR | 1020070054761 | 5/2007 |
| KR | 101097399 | 12/2011 |
| WO | 95/02358 A1 | 1/1995 |
| WO | 95/12348 A1 | 5/1995 |
| WO | 0014545 A1 | 3/2000 |
| WO | 00/26721 A1 | 5/2000 |
| WO | 2006/009906 A2 | 1/2006 |
| WO | 2006009910 A2 | 1/2006 |
| WO | 2011/159148 A2 | 12/2011 |

OTHER PUBLICATIONS

International Search Report for PCT/US2005/21594 mailed Apr. 3, 2007.

* cited by examiner

TRANSMITTED LIGHT DETECTION TYPE MEASUREMENT APPARATUS FOR SKIN AUTOFLUORESCENCE

CROSS-REFERENCE TO RELATED APPLICATION

This application claims under 35 U.S.C. §119(a) the benefit of Korean Patent Application No. 10-2012-0028724 filed Mar. 21, 2012, and Korean Patent Application No. 10-2012-0074251 filed Jul. 9, 2012, the entire contents of which are incorporated herein by reference.

BACKGROUND (a) Technical Field

The present invention relates to a skin autofluorescence measuring apparatus for diagnosing various diseases such as diabetes, by measuring autofluorescence of the skin from Advanced Glycation End-products (AGEs) accumulated in the skin.

(b) Background Art

The present invention relates to a skin autofluorescence measuring apparatus for diagnosing various diseases, by measuring skin autofluorescence from substances accumulated in the skin.

The autofluorescence is the emission of light from the skin after excitation light is absorbed into the skin. Since having the biometric data inside the skin, the autofluorescence serves as a biomarker of diseases, and enables checking of the damage of physiological state of all body organs by a non-invasive method.

For example, Advanced Glycation End-products (AGEs) are formed via glycoxidation of proteins in human body as a result of Maillard reaction which impairs the functioning of many proteins. In general, exposure to cardiac risk factors such as smoking, intake of high fatty acid containing foods, hypercholesterolemia, and oxidative stress due to acute diseases such as sepsis lead to generation of AGEs. Thus produced AGEs are slowly decomposed and accumulated over a long period of time in the body. An increase in AGEs production is associated with the progress of chronic diseases such as atherosclerosis. With the aging process, AGEs tend to accumulate in the body throughout a person's life.

During continuation of hyperglycemia, continual reactions of non-enzymatic protein glycation and glycoxidation occur, and thus AGEs that are a complex of irreversible glycogen and protein are formed. Accumulation of AGEs rapidly progresses in patients suffering from diabetes, renal failure and cardiovascular diseases. AGEs are accumulated in various tissues including skin. AGEs have the characteristics of irradiating autofluorescence (AF) at a range of blue spectrum (peak near about 440 nm) by excitation light irradiation of the ultraviolet range (peak near about 370 nm)

AGEs can be used as a bio marker regarding a series of diseases, and enable to evaluate physiological damages of the whole body organs by measuring autofluorescence of skin using a non-invasive method. That is, AGEs can predict long-term complications in age-related diseases. In particular, the quantity of skin autofluorescence increases in patients suffering from diabetes and renal failure, and relates to the progress of vascular complications and Coronary Heart Disease (CHD). The AGE accumulation can be measured by skin autofluorescence by a non-invasive method, a non-invasive clinical tool useful for the risk evaluation of long-term vascular complications under environments associated with the accumulation of AGEs and diabetes.

US Patent Application Publication No. 2004-186363 (hereinafter, referred to as Reference 1) discloses technology of evaluating AGEs by measuring skin fluorescence near the forearm of a patient as a method and apparatus that are proposed for AGE evaluation using skin autofluorescence measurement.

In Reference 1, an excitation light source is a blacklight fluorescent tube that emits light in a UV wavelength range of about 300 nm to about 420 nm. The collection and recording of light are performed by an optical fiber spectrometer. In order to increase a measurement area, the end surface of an optical fiber is disposed apart from a transparent window of the apparatus by a certain distance (d is about 5 mm to about 9 mm). In order to reduce an influence of light reflected from skin and window, the optical fiber is disposed oblique to the surface of the window at about 45 degrees.

Specifically, in Reference 1, the end surface of the optical fiber for collecting light is disposed as distant as possible from a target spot. In this case, the area of the target spot to be measured is about 0.4 cm$^2$.

However, there is a limitation in the above method that a fluorescent signal that is collected is considerably reduced as the measurement distance (d) increases to increase the measurement area of the target spot. Accordingly, in Reference 1 according to a related art, the reliability of data detection may be reduced due to a limitation of the size of the skin area that can be measured. Particularly, such an accuracy limitation is considerably represented in parts such as moles, vessels, and wounds that are heterogeneous spots of skin.

Meanwhile, US Patent Application Publication No. 2008-103373 (hereinafter, referred to as Reference 2) discloses an apparatus for measuring AGEs to perform a screen test of a diabetic. Similarly to Reference 1, the apparatus disclosed in Reference 2 includes an optical fiber spectrometer to perform fluorescence measurement on the forearm skin. However, unlike in Reference 1, optical fiber probes are provided in a form of bundle including multiple branches.

In the apparatus of Reference 2, ultraviolet light and blue light emitting from light-emitting diodes are irradiated on the forearm of a subject through optical fiber probes, and skin fluorescence and diffusion reflection light emitting therefrom are collected through the probes. The collected light is wavelength-dispersed in a spectrometer, and then detected by a linear array detector. Two branches (illumination fibers; channel 1 and channel 2) of the optical fiber probe serve to irradiate light on a target spot, and a third branch (collection fibers) delivers light from the target to a multi-channel spectrometer. The end surface of a tissue interface, where the branch bundles of the optical fiber probes are combined, becomes in contact with skin to be irradiated.

Light from a white light LED is emitted from one branch of the optical fiber probe for reflection light spectrum measurement, and light from an appropriate LED among LEDs emitting light of ultraviolet to a blue light spectrum range is emitted from another branch of the optical fiber probe via a switching apparatus. Various wavelengths can be selected to select optimal fluorescence excitation conditions. The reflection light spectrum measurement is used to detect autofluorescence generated due to melanin and hemoglobin and compensate for the measurement result. Respective optical fibers are disposed in the optical fiber bundle by a certain sequence. Optical fibers from three branches of the optical fiber bundle are sequentially disposed in a mosaic pattern at an interval of b=0.5 mm.

In Reference 2, since light is irradiated on the forearm of a subject through an optical fiber probe, the optical fiber probe is included as an optical-transmission medium. However, the optical fiber probe has a limitation in delivery loss which occurs according to the small diameter and low numerical aperture of optical fibers Additionally, since both apparatuses disclosed in References 1 and 2 include optical fibers in a light-receiving unit that receives light, there is an inherent limitation in the optical fiber probe of the light-receiving unit. Since References 1 and 2 are configured to use an optical fiber spectrometer and a linear array detector, there is a limitation in that the autofluorescence signal wavelength of AGE becomes relatively smaller in a detection area that is occupied by the linear array detector. Accordingly, a detected fluorescence signal is dispersed, and the light intensity of a wavelength to be detected by the linear array detector becomes relatively smaller. Also, due to the optical fiber probe and optical fiber spectrometer, it is difficult to minimize facilities.

Meanwhile, when the skin fluorescence is measured to diagnose diseases, a transmitted light detection method may be considered to detect transmitted light of light irradiated on the skin and skin fluorescence at a location where the transmitted light is measured, in addition to a reflection detection method of detecting reflected light and skin fluorescence at a region where light irradiated on the skin is reflected.

In the transmitted light detection method, the target skin measured for the intensity of the inherent fluorescence generated from the skin is transmitted by irradiation light such that light can be detected at the opposite side of the target skin.

Generally, parts of the target skin can be considered by the transmitted light detection method as follows. First, in case of the earlobe having a thickness of about 3 mm, the loss of transmitted light is considerable, and an influence of blood absorbing light is very considerable. Also, in case of fingers, the measurement is considerably affected by fluorescence generated from the fingernails when the measurement is performed between the fingernails and the skin across the fingernails. On the other hand, when the measurement is performed between the fingernails and the skin at the opposite side thereof in an orthogonal direction to the fingernails, an optical path and the loss ratio increase, and the measurement is considerably affected by finger skin condition and blood. Meanwhile, there are the following advantages when the measurement is performed on a skin between the thumb and the index finger. First, since the thickness of the skin is about 1 mm, the optical loss is not great. Second, the measurement is little affected by blood. Third, the measurement is little affected by skin pigments, and is convenient to perform.

Meanwhile, although selective diagnosis using transmitted light is performed on body parts, the intensity of the fluorescence generated from the skin is affected by the light scattering and absorption occurring inside the skin as well as fluorescence substances included in the skin.

Therefore, since a measurement error occurs due to the influences of the light scattering and absorption, it is necessary to correct the measurement error in order to exactly detect the skin fluorescence due to the fluorescence excitation. Particularly, in case of diagnosing diseases such as diabetes using the skin fluorescence measurement values, since a value difference between persons with diseases and persons without diseases is not great enough to offset the measurement error, an apparatus of more exactly detecting a skin fluorescence signal is needed even when the skin fluorescence is measured by the transmitted light detection method.

Therefore, for implementing the selective diagnosis apparatus using the transmitted light detection method, the miniaturization and the mobility of the apparatus has to be first prepared. Accordingly, the efficiency of light irradiation and fluorescence detection in the apparatus is needed.

Also, it is very important to improve the efficiency of the light irradiation and the fluorescence detection and reduce a measurement error due to the light scattering and absorption inside the skin in order to achieve an exact diagnosis on selective diagnosis parts for more clearly discriminating between persons with diseases and persons without diseases.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention provides a transmitted light detection type measurement apparatus for skin fluorescence, which can detect skin fluorescence together with transmitted and calculate a corrected skin fluorescence signal with improved accuracy from the detected skin fluorescence and the transmitted light of irradiation, in measuring Advanced Glycation End products (AGEs) fluorescence from the skin.

The present invention also provides a transmitted light detection type measurement apparatus for skin fluorescence, which can increase a diagnosis possibility of diseases such as diabetes by exactly evaluating diagnosis factors such as AGEs from corrected skin fluorescence values.

The present invention also provides a transmitted light detection type measurement apparatus for skin fluorescence, in which an optical system and a light source system can be simply configured to conveniently perform a diagnosis process.

In one aspect, the present invention provides a transmitted light type measurement apparatus for skin fluorescence, which is configured to perform light irradiation and light detection on a reference sample and a measurement target, the apparatus including: a first light source irradiating excitation light; a second light source irradiating light of a wavelength different from that of light from the first light source; a first optical detector and a second optical detector that are disposed to detect transmitted light from the first light source and the second light source and disposed to detect two different wavelengths with respect to a fluorescence signal and a transmitted light signal; a light source switching controller for controlling turning on/off of the first light source and the second light source; and an operator calculating a corrected skin fluorescence signal from the fluorescence signal and the transmitted light signal detected by the first optical detector and the second optical detector, wherein the second light source irradiates light of the same wavelength range as skin fluorescence excited by the excitation light from the first light source and emitted.

In an exemplary embodiment, the light source switching controller may control the first light source and the second light source such that turning-on states of the first light source and the second light source are separated from each other in time.

In another exemplary embodiment, the switching controller may be configured to detect the fluorescence signal and the transmitted light signal from the first light source and the transmitted light signal from the second light source while continuously repeating a process of sequentially turning on and off the first light source and the second light source.

In still another exemplary embodiment, the measurement target and the reference sample may be selectively located on optical paths of the first light source and the second light source.

In yet another exemplary embodiment, the first light source may irradiate light with a wavelength of 370±20 nm.

In still yet another exemplary embodiment, the second light source may irradiate light with a wavelength of 440±20 nm.

In a further exemplary embodiment, the switching controller may control all the first light source and the second light source to be turned off before turning on each of the light sources.

In another further exemplary embodiment, when the switching controller turns off all the first light source and the second light source, the first optical detector and the second optical detector may measure dark signals, and the operator may store the measured dark signals and compensate for the fluorescence signal and the transmitted light signal detected from the stored dark signals.

In still another further exemplary embodiment, the switching controller may control the first light source and the second light source to repeat turning on/off at a period of about 10 Hz to about 100 Hz.

In yet another further exemplary embodiment, the apparatus may further include an optical detector switching controller for controlling turning on/off of the first optical detector and the second optical detector.

In still yet another further exemplary embodiment, the apparatus may include an optical sensor including the first light source, the second light source, the first optical detector, and the second optical detector; and a main body electrically connected to the optical sensor and including the operator, wherein the optical sensor is detachable from the main body.

In a still further exemplary embodiment, the optical sensor may include a first fixing part connected to the first light source and the second light source and a second fixing part connected to the first optical detector and the second optical detector, and the first and second fixing parts may face each other to form an insertion space therebetween.

In a yet still further exemplary embodiment, the optical sensor may include a memory for storing detected data.

In a yet still further exemplary embodiment, the optical sensor may include a common light source light guide for transmitting light irradiated from the first light source and the second light source in a shared manner.

In a yet still further exemplary embodiment, the optical sensor may include a common detection light guide for transmitting the transmitted light and the skin fluorescence to the first optical detector and the second optical detector in a shared manner.

In a yet still further exemplary embodiment, the optical sensor may include a first dichroic mirror on an optical path to transmit light irradiated from the first light source and the second light source to the common light source light guide.

In a yet still further exemplary embodiment, the optical sensor may include a second dichroic mirror on an optical path to divide light from the common detection light guide and transmit the divided light to the first optical detector and the second optical detector.

In a yet still further exemplary embodiment, the apparatus may comprise a light source filter between the first light source and the first dichroic mirror to pass light of a first wavelength irradiated from the first light source and inhibit light of a second wavelength irradiated from the second light source.

In a yet still further exemplary embodiment, the apparatus may comprises objective lenses between the first and second light sources and the first dichroic mirror to condense light irradiated from the first and second light sources, respectively.

In a yet still further exemplary embodiment, the apparatus may include a first detection filter between the second dichroic mirror and the first optical detector and a second detection filter between the second dichroic mirror and the second optical detector, wherein the first detection filter passes light of a first wavelength and inhibits light of a second wavelength, and the second detection filter inhibits light of the first wavelength and passes light of the second wavelength.

In a yet still further exemplary embodiment, the apparatus may include objective lenses between the first and second optical detectors and the second dichroic mirror to concentrate light passing the second dichroic mirror on the first optical detector and the second optical detector, respectively.

In a yet still further exemplary embodiment, the apparatus may include a first light source light guide for transmitting light irradiated from the first light source and a second light source light guide for transmitting light irradiated from the second light source.

In a yet still further exemplary embodiment, the optical sensor may include a first detection light guide for transmitting the transmitted light of the first light source to the first optical detector and a second detection light guide for transmitting the transmitted light of the second light source or the skin fluorescence to the second optical detector.

In a yet still further exemplary embodiment, the apparatus may include an light source filter between the first light source and the first light source light guide to pass light of a first wavelength irradiated from the first light source and inhibit light of a second wavelength irradiated from the second light source.

In a yet still further exemplary embodiment, the apparatus may include a first detection filter between the first light source light guide and the first optical detector to pass light of a first wavelength and inhibit light of a second wavelength, and a second detection filter between the second light source light guide and the second optical detector to inhibit light of the first wavelength and pass light of the second wavelength.

In a yet still further exemplary embodiment, the first light source and the second light source may be disposed at a distal end of the first fixing part to directly irradiate light on the measurement target, and the first optical detector and the second detector may be disposed at a distal end of the second fixing part to directly detect the transmitted light and the skin fluorescence.

In a yet still further exemplary embodiment, the first optical detect and the second optical detector may be configured to form two sectors, and may include band-pass filters at the front of the two sectors to divide light into a first wavelength ($\lambda 1$)) and a second wavelength ($\lambda 2$), respectively.

In a yet still further exemplary embodiment, the first fixing part and the second fixing part may be manufactured in a form of clip to fix the measurement target while compressing the measurement target.

In a yet still further exemplary embodiment, the reference sample may be movably mounted in the optical sensor, and may be loaded into the insertion space when the measurement target is removed from the insertion space between the first fixing part and the second fixing part.

In a yet still further exemplary embodiment, the optical sensor may perform measurement on a skin when the skin that is the measurement target is located at the insertion space, and may perform measurement on the reference sample when the measurement target is removed and then the reference sample is located at the insertion space.

In a yet still further exemplary embodiment, the optical sensor may store measured results about the skin that is the measurement target T and the reference sample, and may transmit stored data about the skin and reference sample to the main body to allow the operator to calculate the corrected skin fluorescence signals.

In a yet still further exemplary embodiment, the main body further may include a display part, and the display part outputs the corrected skin fluorescence signals calculated in the operator.

In a yet still further exemplary embodiment, the operator may calculate a skin fluorescence value corrected by the following equation:

$$AF_{corr}=K[I(\lambda 2,t1)/I_0(\lambda 2,t1)]/\{[T(\lambda 1)]^{k1}[T(\lambda 2)]\}^{k2}$$

(here, $T(\lambda 1)=I(\lambda 1,t1)/I_0(\lambda 1,t1)$: Diffuse reflection coefficient in excitation wavelength;

$T(\lambda 2)=I(\lambda 2,t2)/I_0(\lambda 2,t2)$: Diffuse reflection coefficient in emission wavelength;

$I(\lambda 2,t1)$: Inherent fluorescence (skin fluorescence) signal value of skin tissue;

$I(\lambda 1,t1)$: Transmitted light signal value of skin tissue in excitation light wavelength;

$I(\lambda 2,t2)$: Transmitted light signal value of skin tissue in emission light wavelength;

k1, k2: Exponents of correction function with respect to excitation light and emission light wavelength;

$I_0(\lambda 2,t1)$: Inherent fluorescence signal value of reference sample;

$I_0(\lambda 1,t1)$: Transmitted light signal value of reference sample in excitation light wavelength; and $I_0(\lambda 2,t2)$: Transmitted light signal value of reference sample in emission light wavelength).

K: Ratio coefficient that considers the features of the used reference samples.

Other aspects and exemplary embodiments of the invention are discussed infra.

In a yet still further exemplary embodiment, the present invention provides a transmitted light detection type measurement apparatus for skin fluorescence, comprising: a light source irradiating excitation light; an optical detector for detecting transmitted light and fluorescence signals regarding the excitation signal irradiated from the light source; and a pair of optical transmitters configured to transmit the excitation light irradiated from the light source to a measurement target and transmit the transmitted light and fluorescence signals to the optical detector; wherein the optical transmitters have a mounting surface mounted with the light source or the optical detector, a reflection surface extending from the mounting surface to the measurement target and reflecting light, and a contact surface connected such that light is incident to the measurement target.

In a yet still further exemplary embodiment, the light source may be configured to comprise a first light source irradiating excitation light and a second light source irradiating light having a wavelength different from that of light from the first light source. The optical detector may be configured to comprise a first optical detector and a second optical detector that are disposed to detect two different wavelengths with respect to a fluorescence signal and a reflected light signal.

In a yet still further exemplary embodiment, the second light source may irradiate light with a wavelength range of a skin fluorescence excited and emitted by the excitation light from the first light source.

In a yet still further exemplary embodiment, the apparatus may further include: a light source switching controller for controlling turning on/off of the first and second light sources; and an operator calculating a corrected skin fluorescence signal from the fluorescence signal and the transmitted light signal detected by the first optical detector and the second optical detector.

In a yet still further exemplary embodiment, the pair of optical transmitters may include a first optical prism connected to the light source and a second optical prism connected to the optical detector.

In a yet still further exemplary embodiment, the first optical prism and the second optical prism may be triangular prisms having a triangular section.

In a yet still further exemplary embodiment, the first optical prism may have a mounting surface mounted with a first light source and a reflection surface mounted with a second light source.

In a yet still further exemplary embodiment, the second optical prism may have a mounting surface mounted with a first optical detector and a reflection surface mounted with a second optical detector.

In a yet still further exemplary embodiment, the pair of optical transmitters may include a first optical pipe connected to the light source and a second optical pipe connected to the optical detector.

In a yet still further exemplary embodiment, the first optical pipe and the second optical pipe may have reflection surfaces that are inclined, and have a tapered pillar shape in which a mounting surface is wider than a contact surface.

In a yet still further exemplary embodiment, the first optical pipe may have a mounting surface mounted with a first light source and a second light source.

In a yet still further exemplary embodiment, the second optical pipe may have a mounting surface mounted with a first optical detector and a second optical detector.

In a yet still further exemplary embodiment, the apparatus may further include a dichroic prism at a side of the mounting surface of the second optical pipe for dividing detected light into two wavelength bands.

In a yet still further exemplary embodiment, the first optical detector may be disposed to detect reflected light from the dichroic prism, and the second optical detector may be disposed to detect transmitted light from the dichroic prism.

In a yet still further exemplary embodiment, the first optical pipe and the second optical pipe may be vertical-type optical pipes that extend in a perpendicular direction to the contact surface with the measurement target.

In a yet still further exemplary embodiment, wherein the first optical pipe and the second optical pipe may be horizontal-type optical pipes that extend in a parallel direction to the contact surface with the measurement target.

In a yet still further exemplary embodiment, the reflection surfaces of the first optical pipe and the second optical pipe may be tapered such that a cross-sectional area thereof is reduced from the mounting surface to the contact surface.

In a yet still further exemplary embodiment, the mounting surfaces of the first optical pipe and the second optical pipe may be inclined to the reflection surface thereof.

In a yet still further exemplary embodiment, the reflection surfaces of the first optical pipe and the second optical pipe may include a bent reflection surface that is inclined to the contact surface, respectively.

In a yet still further exemplary embodiment, the reflection surfaces of the first optical pipe and the second optical pipe may be processed by mirror coating.

In a yet still further exemplary embodiment, the apparatus may further include: a transfer part for moving the optical transmitter in a vertical direction; and a thickness indicator measuring a distance between the two optical transmitters and indicating a thickness of the measurement target.

In a yet still further exemplary embodiment, the apparatus may further include an optical connector disposed over the contact surface of the optical transmitter and contacting the measurement target.

In a yet still further exemplary embodiment, the optical connector may serve as a connection layer formed of a liquid material or an elastic material between the optical transmitter and the measurement target.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

Figure 1:
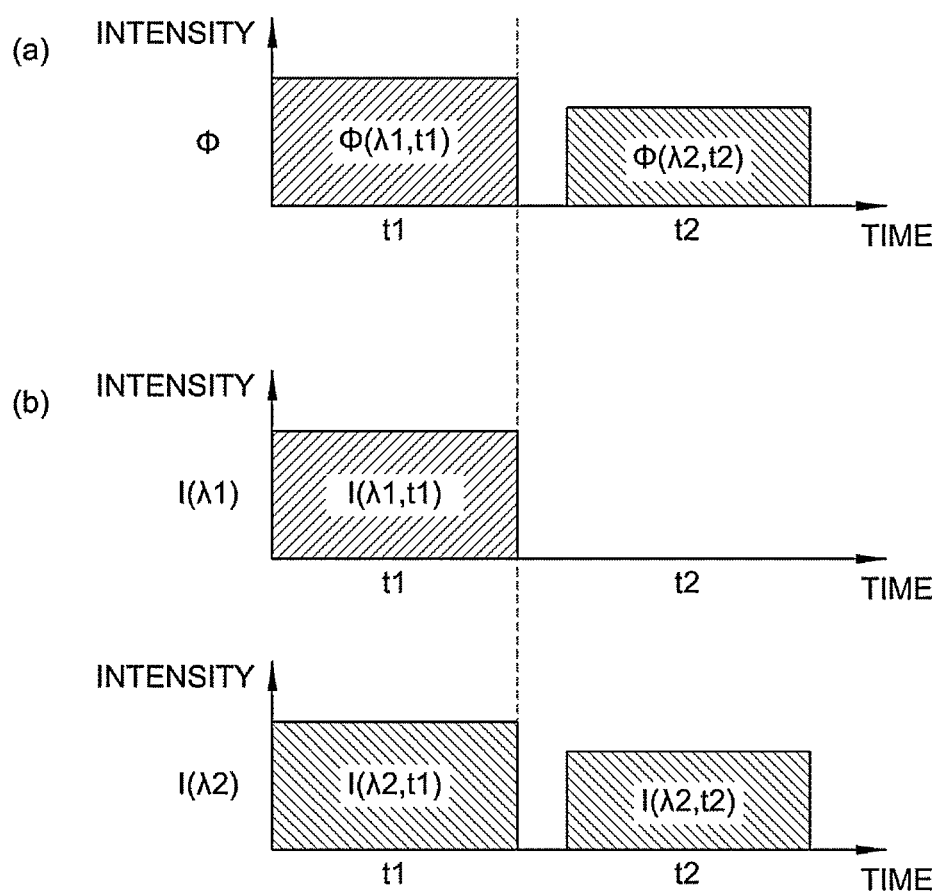
FIG. 1 is a graph illustrating the intensities of light inputted from a light source and light detected by an optical detector which are shown according to time to explain the measurement principle of a transmitted light detection type measurement apparatus for skin fluorescence according to an embodiment of the present invention.

Reference numerals set forth in the Drawings includes reference to the following elements as further discussed below:

| | |
|---|---|
| 100: optical sensor | 200: main body |
| 111: first light source | 112: second light source |
| 113: first dichroic mirror | 114: light source filter |
| 115, 116: objective lens | 117: common light source light guide |
| 121: first optical detector | 122: second optical detector |
| 123: second dichroic mirror | 124: first detection filter |
| 125: second detection filter | 126, 127: objective lens |
| 128: common detection light guide | 130: electronic control module |
| 131, 132: A/D converter | 133: data transfer module |
| 134: driver module | 210: operation part |
| 220: display part | |
| 300: optical sensor | 400: main body |
| 311: first light source | 312: second light source |
| 313: light source filter | 314: first light source light guide |
| 315: second light source light guide | 321: first optical detector |
| 322: second optical detector | 323: first detection filter |
| 324: second detection filter | 325: first detection light guide |
| 326: second detection light guide | 330: electronic control module |
| 331, 332: A/D converter | 333: data transfer module |
| 334: driver module | 410: operation part |
| 420: display part | |
| 511: first light source | 512: second light source |
| 521: first optical detector | 522: second optical detector |
| 530: electronic control module | 531, 532: A/D converter |
| 533: data transfer module | 534: driver module |
| 600: main body | 610: operation part |
| 620: display part | |
| 710: first light source | 712: second light source |
| 720: first optical prism | 730: second optical prism |
| 741: first optical detector | 742: second optical detector |
| 750: optical connector | 761, 762: filter |
| 800: optical sensor | |
| 811: first light source | 812: second light source |
| 820: first optical pipe | 830: second optical pipe |
| 841: first optical detector | 842: second optical detector |
| 850: optical connector | 860: main body |
| 870: dichroic prism | |
| 911: first light source | 912: second light source |
| 920: first optical pipe | 930: second optical pipe |
| 941: first optical detector | 942: second optical detector |
| 950: optical connector | |
| T: measurement target (skin) | R: reference sample |

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The above and other features of the invention are discussed infra.

The present invention relates to a skin fluorescence measurement apparatus for irradiating excitation light on the skin and measuring skin fluorescence generated by the excitation light for the purpose of diagnosis of diseases such as diabetes. Particularly, it provides a transmitted light detection type measurement apparatus for skin fluorescence, which can exactly measure corrected skin fluorescence data from skin fluorescence data at a location where transmitted light of irradiation light and the transmitted light are detected from skin fluorescence scattered and emitted from the inside of the skin due to the irradiation light on the skin.

For this, a sequential measurement may be performed on a target to be diagnosed and a reference sample, and information obtained from the target may be compared with information obtained by the reference sample to remove an individual deviation that the target has, while a light source and an optical detector may be sequentially turned on/off according to certain conditions required in the above process. Thus, provided is a transmitted light detection type measurement apparatus for skin fluorescence that can provide a corrected skin fluorescence value.

Hereinafter, exemplary embodiments of a transmitted light detection type measurement apparatus for skin fluorescence will be described in detail with reference to the accompanying drawings.

It is necessary to select a skin target for measurement of fluorescence generated on the skin and consider factors that affect the measured fluorescence. The measured fluorescence may depend on light scattering and absorption occurring inside the skin as well as fluorescent substances included in the skin. Particularly, it is necessary to correct measured fluorescence values in consideration of influences of light absorption and scattering in the fluorescence wavelength generated in fluorescent substances and the excitation light wavelength irradiated to excite fluorescent substances. Accordingly, the following empirical Equation (1) may be considered to reduce the influence of optical factors on the fluorescent intensity.

$$AF_{corr}=AF/(T_1^{k1}T_2^{k2}) \quad (1)$$

Here, a corrected fluorescence value $AF_{corr}$ may be obtained by dividing a measured fluorescence value AF by an excitation diffusion transmitted light T1 and a diffusion transmitted light T2 of emission in the fluorescent wavelength range. The two diffusion transmitted light values may be adjusted by exponents k1 and k2 without a degree.

In an exemplary embodiment of the present invention, Equation (1) may be used to obtain the corrected skin fluorescence value to obtain a corrected skin fluorescence value by a transmitted light detection method, and concrete values may be introduced to obtain the corrected skin fluorescence value through an actual test.

$I(\lambda 2,t1)$: Inherent fluorescence (skin fluorescence) signal value of skin tissue $I(\lambda 1,t1)$: Transmitted light signal value of skin tissue in excitation light wavelength $I(\lambda 2,t2)$: Transmitted light signal value of skin tissue in emission light wavelength k1, k2: Exponents of correction function with respect to excitation light and emission light wavelength The corrected skin fluorescence value that is newly induced by the transmitted detection method may be expressed as Equation (2).

$$AF_{tissue}=[I(\lambda 2,t1)]/[I(\lambda 1,t1)^{k1}I(\lambda 2,t2)^{k2}];k1,k2<1 \quad (2)$$

where $AF_{tissue}$ is a correction signal of an inherent fluorescence of a skin tissue.

The light measurement may be periodically performed at different time intervals t1 and t2. The measurement results may be averaged to increase the accuracy. The measured values may be recorded in a form of time diagram to trace the variation at an appropriate time.

Meanwhile, correction of deviations depending on equipment and correction measurement for a comparison between the results obtained from different samples may be needed. Accordingly, in the present invention, the equal measurement may be performed by introducing reference samples together with the measurement of the target skin tissue. In order to increase the measurement accuracy, the fluorescence intensity $I_0(\lambda 2, t1)$ and the transmitted light signal values $I_0(\lambda 1, t1)$ and $I_0(\lambda 2, t2)$ in the excitation light and the emission light may be similar to the optical characteristics of the skin.

The signal values generated in the measurement process of the introduced reference sample may be expressed as follows similarly to those for the target skin tissue.

$I_0(\lambda 2,t1)$: Inherent fluorescence signal value of reference sample.

$I_0(\lambda 1,t1)$: Transmitted light signal value of reference sample in excitation light wavelength.

$I_0(\lambda 2,t2)$: Transmitted light signal value of reference sample in emission light wavelength.

The signals obtained from the reference samples may be processed by Equation (3) similarly to Equation (2).

$$AF_{reference}=[I_0(\lambda 2,t1)]/[I_0(\lambda 1,t1)^{k1}I_0(\lambda 2,t2)^{k2}] \quad (3)$$

A result obtained by dividing $AF_{tissue}$ by $AF_{reference}$ may be normalized, and a finally corrected inherent fluorescence value may be expressed as Equation (4).

$$AF_{corr}=K(AF_{tissue}/AF_{reference}) \quad (4)$$

$$AF_{corr}=K[I(\lambda 2,t1)/I_0(\lambda 2,t1)]/\{[(\lambda 1,t1)/I_0(\lambda 1,t1)]^{k1}[I(\lambda 2,t2)/I_0(\lambda 2,t2)]\}^{k2} \quad (5)$$

where K is a ratio coefficient that considers the features of the used reference samples.

Equation (5) may be simplified as Equation (6).

$$AF_{corr}=K[I(\lambda 2,t1)/I_0(\lambda 2,t1)]/\{[T(\lambda 1)]^{k1}[T(\lambda 2)]\}^{k2} \quad (6)$$

$T(\lambda 1)=I(\lambda 1,t1)/I_0(\lambda 1,t1)$: Diffuse transmission coefficient in excitation wavelength.

$T(\lambda 2)=I(\lambda 2,t2)/I_0(\lambda 2,t2)$: Diffuse transmission coefficient in emission wavelength.

Thus, regarding the transmitted light detection type measurement apparatus of skin fluorescence according to the embodiment of the present invention, the corrected skin fluorescence values may be calculated by the above operation processes.

In this regard, the principle proposed for the measurement will be described in detail with reference to FIG. 1.

FIG. 1 is a graph illustrating the intensities of light inputted from a light source and light detected by an optical detector which are shown according to time to explain the measurement principle of a transmitted light detection type measurement apparatus for skin fluorescence according to an embodiment of the present invention. As shown in FIG. 1, in the transmitted light detection type measurement apparatus for skin fluorescence, the measurement may be successively performed under a first condition in which light corresponding to a wavelength range (first wavelength $\lambda 1$) of excitation light is irradiated as an input, and a second condition in which light corresponding to a wavelength range (second wavelength $\lambda 2$) of skin fluorescence generated by the excitation light is irradiated while being separated from each other in time. The wavelength range of the irradiation light corresponding to the first and second conditions may be selectively configured according to the skin fluorescence to be detected. For example, considering that the skin fluorescence is detected with respect to AGE in an exemplary embodiment, light with the first wave length of 370 nm±20 nm may be used as the excitation light for the fluorescence excitation under the first condition, and light with the second wave length of 440 nm±20 nm corresponding to the wavelength of the skin fluorescence with respect to AGE may be selectively used under the second condition.

The measurement may be performed using an optical sensor including light sources for emitting two different wavelengths of light and an optical detector for detecting two different wavelengths of light. The measurement may be performed by contacting the optical sensor with the skin tissue corresponding to a measurement target in the diagnosis observance process or the reference sample in the correction process.

In regard to the measurement process, FIG. 1A shows an operating time diagram showing the respective light sources with respect to two different wavelengths operate while being separated from each other in time. In this case, light $\Phi(\lambda 1, t1)$ irradiated from a first light source that is an excitation light source may be configured to exist in a different time from light $\Phi(\lambda 2, t2)$ from a second light source that is a reference light source of different wavelength range.

FIG. 1B shows an operating time diagram with respect to two optical detectors. In the same time while light $\Phi(\lambda 1,t1)$ is being radiated from the first light source, two signals may be generated with respect to the excited skin fluorescence and the transmitted light. Two signals generated in the excitation light wavelength may be a transmitted light signal $I(\lambda 1,t1)$ and an excited fluorescence signal $I(\lambda 2, t1)$.

Meanwhile, only a single signal may be generated in a time when light $\Phi(\lambda 2,t2)$ is irradiated from the second light source. The signal generated by the second light source may be only a transmitted light signal $I(\lambda 2,t2)$ in the wavelength range of the irradiated light.

As shown in FIG. 1, in the transmitted detection type measurement apparatus for skin fluorescence, the light irradiation of the first light source and the light irradiation of the second light source may be sequentially performed on the measurement target while being separated from each other in time. In this case, the signals detected from the optical detector may be collected upon each light irradiation, and then may be calculated using the above equations to output the corrected skin fluorescence value.

Figure 2:
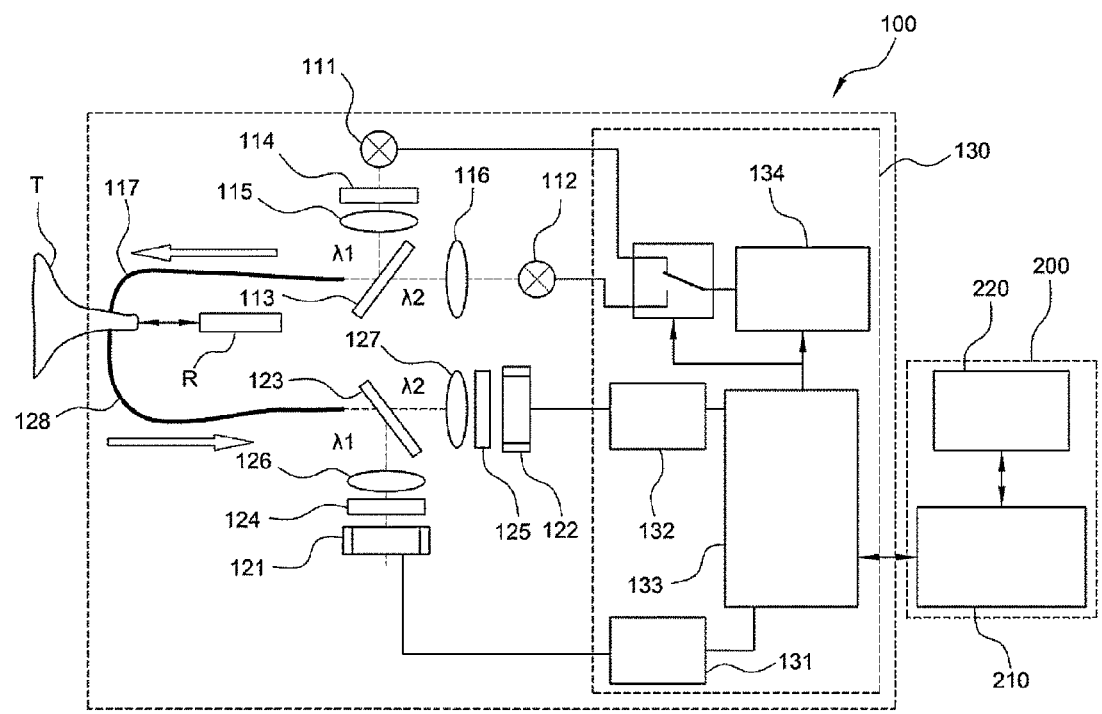
FIG. 2 is a view illustrating a transmitted light detection type measurement apparatus for skin fluorescence according to an embodiment of the present invention.
Figure 3:
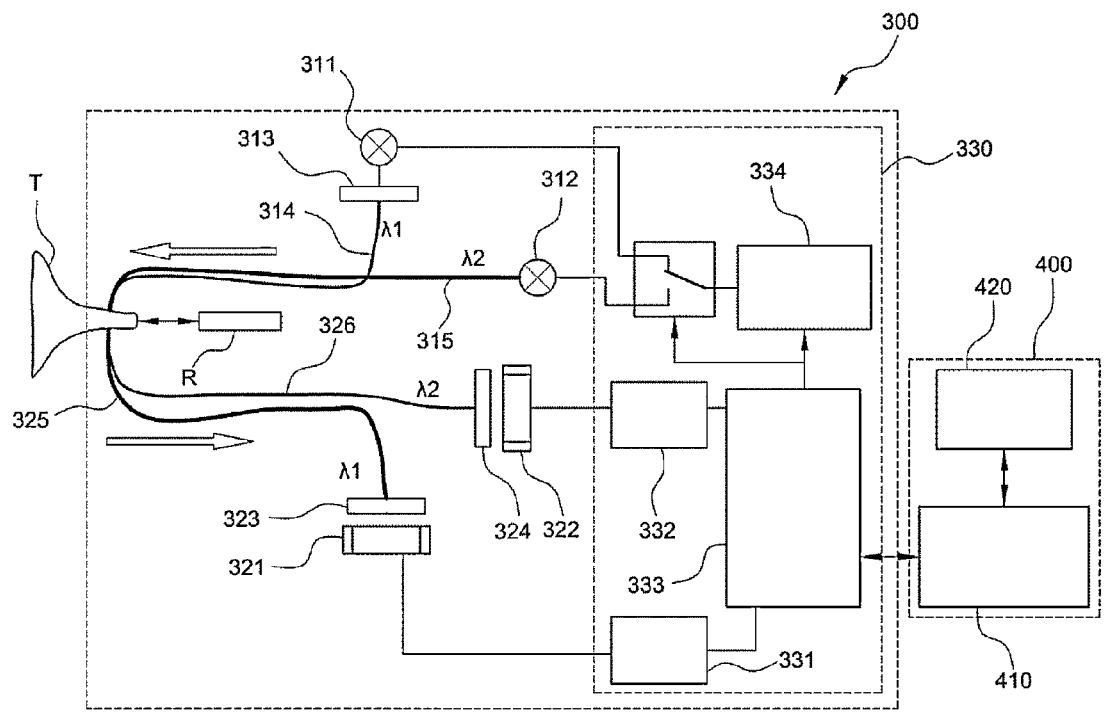
FIG. 3 is a view illustrating an exemplary arrangement of light sources and optical detectors when there is no gap between the light sources and the optical detectors and a target skin in a transmitted light detection type measurement apparatus for skin fluorescence according to an embodiment of the present invention.
Figure 4:
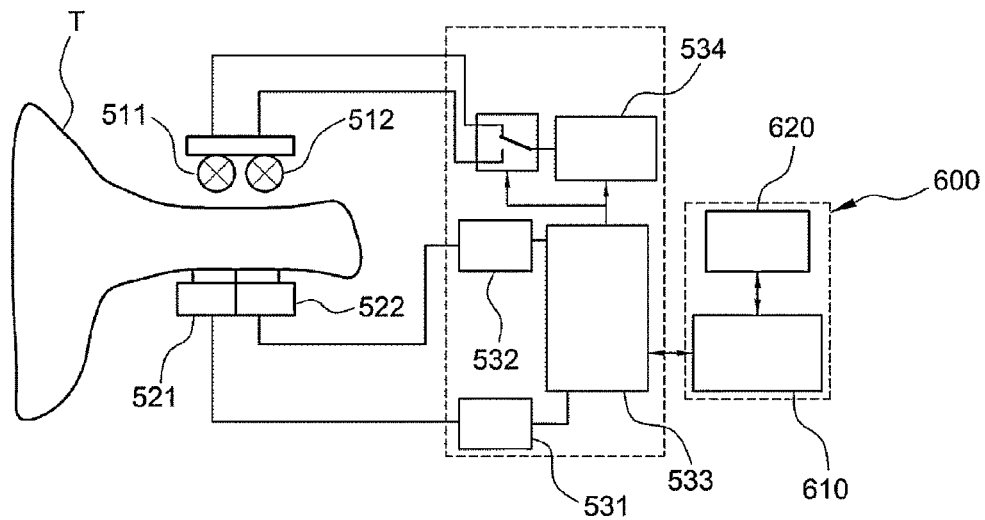
FIG. 4 is a view illustrating an exemplary arrangement of light sources and optical detectors when there is a gap between the light sources and the optical detectors and a target skin in a transmitted light detection type measurement apparatus for skin fluorescence according to an embodiment of the present invention.

FIGS. 2 through 4 are views illustrating transmitted light detection type measurement apparatuses for skin fluorescence according to exemplary embodiments of the present invention, which are implemented by the measurement principle described above.

As shown in FIGS. 2 through 4, the transmitted light detection type measurement apparatuses for skin fluorescence may include an optical sensor that irradiates excitation light on the skin and detects skin fluorescence, and a main body that is connected to the optical sensor and analyzes data detected by the optical sensor to display the data.

However, it will be only an exemplary configuration that the optical sensor and the main body are configured to be separated from each other. Accordingly, if necessary, the transmitted light detection type measurement apparatus for skin fluorescence may be manufactured in a form of a single sensor without a separate main body, or may further include other components connected thereto.

The transmitted light detection type measurement apparatus for skin fluorescence may be configured to include a light source and an optical detector to irradiate light on a target to be measured and detect skin fluorescence generated by the irradiated light.

Particularly, in order to provide exact skin fluorescence values by correcting the detected skin fluorescence values, the transmitted light detection type measurement apparatus for skin fluorescence may include two light sources that irradiate different wavelengths of light and two optical detectors that can detect different wavelengths of transmitted light and skin fluorescence generated by the two irradiation lights.

Specifically, the two light sources may include the first light source that emits light corresponding to the wavelength range (first wavelength $\lambda 1$) of the excitation light and the second light source that emits light corresponding to the wavelength range (second wavelength $\lambda 2$) of skin fluorescence generated by the excitation light. The two optical detectors may be disposed at locations where transmitted light of the first light source and the second light source can be detected.

The two optical detectors may include a first optical detector for detecting transmitted light $\lambda 1$ with respect to the excitation light from the first light source and a second optical detector for detecting transmitted light $\lambda 2$ with respect to the emission light from the second light source and the skin fluorescence $\lambda 2$ generated by the excitation light.

Therefore, the two light sources and optical detectors may be disposed at locations where the transmitted light and skin fluorescence can be simultaneously detected. Preferably, the light sources and the optical detectors may be configured to face each other to form a space into which the measurement target or the reference sample can be inserted at the end portion of the optical sensor.

In this case, the light sources and the optical detectors need not face each other. When connected by an optical signal transmission method such as a light guide, an end portion where light irradiation is performed and another end portion where light detection is performed may be disposed to face each other.

Accordingly, in the transmitted light detection type measurement apparatus for skin fluorescence according to the embodiment of the present invention, the light guide may be disposed between insertion spaces where the measurement target is located to allow light to be transmitted to skin that is the measurement target and the reference sample through the light guide. Also, the light guide may also be disposed between the insertion space and the optical detector to allow the transmitted light that transmits the skin and the skin fluorescence to be transmitted to the optical detector through the light guide.

The optical sensor including the light sources and the optical detectors may be configured to perform light transmission to the measurement target and optical signal detection, respectively. For this, the end portion of the optical sensor may be configured to contact the skin that is the measurement target or the reference sample.

The optical sensor may be configured in a form of clips in which an insertion space is formed between a first fixing part at the side of light source from which light is irradiated and a second fixing part at the side of optical detector for detecting light, which are facing each other.

Accordingly, when the measurement target is located in the insertion space between the first fixing part and the second fixing part, light irradiation and light detection are performed on the measurement target.

When there is no measurement target in the insertion space, the reference sample may be inserted into the insertion space, and light irradiation and light detection may be performed on the inserted reference sample. The reference sample may be configured to be automatically inserted into the insertion space. In this case, when the measurement target is removed from the insertion space after the light irradiation and the light detection, the reference sample may be automatically inserted, and then light irradiation and light detection may be performed on the reference sample.

In this case, the reference sample may be selected so as to have the optical characteristics of the diffuse transmission and fluorescence similar to the human body's tissue that is measured.

Meanwhile, the transmitted light detection type measurement apparatus for skin fluorescence may further include a light source switching control unit for controlling turning on/off of the first and second light sources. More preferably, the transmitted light detection type measurement apparatus for skin fluorescence may further include an optical detector switching control unit for controlling turning on/off of the first and second optical detectors.

The light source switching control unit and the optical detector switching control unit may control switching such that the light sources and the optical detectors can exactly operate according to the detection conditions of the skin fluorescence and the transmitted light in order to exactly calculate the skin fluorescence values.

The light source switching control unit may be configured to turn on or off the light sources according to the light irradiation conditions of the transmitted light detection type measurement apparatus for skin fluorescence. For example, under the first condition in which excitation light λ1 is irradiated on the measurement target, the second light source may be turned off and the first light source may be turned on, controlling switching of the light sources such that only the first light source irradiates light of a first wavelength range. On the other hand, under the second condition in which emission light λ2 of a different wavelength range from the excitation light is irradiated on the measurement target, the first light source may be turned off and the second light source may be turned on such that light of a second wavelength range is irradiated from only the second ling source.

Similarly, the optical detector switching control unit may be configured to control turning on/off of the optical detectors according to the measurement conditions. The optical detector switching control unit may be configured to power on/off the optical detectors for detecting light of a wavelength range to be detected under a current measurement condition.

Particularly, since an optical signal with respect to the second wavelength may need to be detected under both first condition in which the excitation light of the first wavelength range is irradiated and second condition in which the emission light of the second wavelength range is irradiated, the second optical detector for detecting light with respect to the second wavelength may be maintained turned on.

In this case, the switching control may be sequentially performed on the light sources for a certain time during the whole measurement process including the first condition and the second condition. In regard to the period of switching with respect to each light source, the switching control may be performed at a high frequency of about 10 Hz to about 100 Hz such that the variation of the diffusion transmittance due to the blood flow does not affect the measurement by considering the pulse rate of the human body. In this process, prior to the light irradiation and the light detection, all light sources may be turned off, and then level evaluation of a dark signal may be performed to automatically compensate for light leaking from the outside.

Also, the transmitted light detection type measurement apparatus for skin fluorescence may include an optical filter selectively disposed at the front of the light source and the optical detector. The optical filter may be disposed on an optical path of the light source such that only light of a desired wavelength range can be irradiated from the light source, or may be disposed at the front of the optical detector such that only light of a wavelength range intended to detect can enter the optical detector.

Meanwhile, the transmitted light detection type measurement apparatus for skin fluorescence may be configured to include the main body that is configured to be connectable to the optical sensor including two light sources and two optical detectors. The main body may be configured to include an operation part that calculates the value of corrected skin fluorescence from data measured by the optical sensor.

The main body may be configured to be wired or wirelessly connected to the optical sensor to receive detected data from the optical sensor, and may be configured to calculate a corrected skin fluorescence value by performing the operation process as described above in the operation part of the main body.

Also, the main body may include a display part to output data about a skin fluorescence signal, and may be configured to output the corrected skin fluorescence signal calculated in the operation part to the outside.

In the transmitted light detection type measurement apparatus for skin fluorescence, when the measurement target is located in the insertion space of the optical sensor, the optical sensor may perform the light irradiation and light detection processes on the measurement target. Thereafter, when the measurement target is removed and then the reference sample is inserted into the insertion space, the light irradiation and light detection processes that have been performed on the measurement target may be similarly performed on the reference sample.

The measured data of the measurement target and the reference sample may be transmitted to the operation part of the main body. The operation part may calculate corrected skin fluorescence values regarding the actual measurement target using data about the fluorescence signals and the reflected light signals that are received. The calculation result may be displayed via the display part on the main body.

The measurement of the measurement target and the reference sample may be repeated at a certain period, and all repeated measurement results may be stored in the optical sensor via a memory. The stored data may be stored in the operation part to perform the operation process for correction. In this case, the repeated measurement results may be averaged to be used in the operation. Preferably, the measurement results may be stored in a form of time diagram to trace the variation of the measurement results.

In this regard, FIG. 2 is a view illustrating a transmitted light detection type measurement apparatus for skin fluorescence according to an exemplary embodiment of the present invention. In FIG. 2, an optical sensor 100 may include a first light source 111 and a second light source 112.

The first light source 111 and the second light source 112 may be configured to transmit light to a measurement target via a common light source light guide 117, and a common detection light guide 128 may be disposed at the opposite side of the common light source light guide 117. Also, the optical sensor 100 may be configured to transmit transmitted light and skin fluorescence to a first optical detector 121 and a second optical detector 122 through the common detection light guide 128.

As shown in FIG. 2, light emitted from the first light source 111 and the second light source 112 may enter the common light source light guide 117 through lenses. In this case, the light sources 111 and 112 may include LEDs, laser diodes, or other light source which can provide light of sufficient brightness within an excitation and emission wavelength range. A light source filter 114 may be disposed between the first light source 111 and the common light source light guide 117 to inhibit light of a second wavelength $\lambda 2$ generated from the second light sources 112. A separate filter may not need to be disposed at the second light source 112. A second detection filter 125 may be disposed at the front of the second optical detector 122. Accordingly, the wavelength range of light emitted from the second light source 112 may be wider than that of light passing the second detection filter 125. For example, a white light LED may be used as the second light source 112.

Light emitted from the first and second light sources 111 and 112 may enter the common light source light guide 117 through a first dichroic mirror 113. In this case, objective lenses 115 and 116 may be disposed between the dichroic mirror 113 and the respective light sources 111 and 112. When the second wavelength $\lambda 2$ is greater than the first wavelength $\lambda 1$, the first dichroic mirror 113 may reflect light of the first wavelength $\lambda 1$ that is short wavelength light, and may pass light of the second wavelength $\lambda 2$ that is long wavelength light. However, the first dichroic mirror 113 may also be configured to pass light of a short wavelength and reflect light a long wavelength. In this case, the locations of the first light source 111 and the second light source 112 need to be switched. Power of the first light source 111 and the second light source 112 may be supplied through switching of a light source switching controller. Preferably, as shown in FIG. 2, power may be supplied via a relay switch in a driver module 134, and power supply to the first light source 111 and the second light source 112 may be alternately performed.

When a measurement target T is located in an insertion space of the optical sensor 100, the optical sensor 100 may perform light irradiation and light detection processes on the measurement target T. Thereafter, when a reference sample R is automatically inserted into the insertion space after the measurement target T is removed, the light irradiation and light detection processes that have been performed on the measurement target T may also be similarly performed on the reference sample R.

Measure data about the measurement target T and the reference sample R may be transmitted to an operation part 210 of a main body 200. The operation part 210 may calculate corrected skin fluorescence values regarding the actual measurement target using data about fluorescence signals and transmitted light signals that are received. The calculation results may be displayed via a display part 220 on the main body 200.

Meanwhile, as shown in FIG. 2, light that has entered the common detection light guide 128 may enter the first optical detector 121 and the second optical detector 122 through an optical system including the objective lenses 126 and 127. A dichroic mirror 123 may be disposed to distribute light into the first optical detector 121 and the second optical detector 122. Similarly to the first dichroic mirror 113, the second dichroic mirror 123 may be configured to reflect light of a short wavelength and pass light of a long wavelength. Also, like in the case where the locations of the first light source 111 and the second light source 112 are switched regarding the first dichroic mirror 113, when the locations of the first optical detector 121 and the second optical detector 122 are switched, transmittance and reflection characteristics of light can be changed to the opposite. In this case, the objective lenses 126 and 127 may serve to effectively concentrate light on the optical detectors 121 and 122, respectively.

Also, filters may be disposed at the front of the optical detectors 121 and 122, respectively. The filters may include a first detection filter 124 and a second detection filter 125. The first detection filter 124 may be disposed at the front of the first optical detector 121, and may be configured to pass a spectrum component of the first wavelength $\lambda 1$ and inhibit a spectrum component of the second wavelength $\lambda 2$. On the other hand, the second detection filter 125 may be disposed at the front of the second optical detector 122, and may be configured to pass the spectrum component of the second wavelength $\lambda 2$ and inhibit the spectrum component of the first wavelength $\lambda 1$.

Meanwhile, the transmitted light detection type measurement apparatus for skin fluorescence according to the embodiment of the present invention may include an Electronic Control Module (ECM) 130 that controls the light irradiation from the light sources in the optical sensor 100 and processes detected optical signals to transmit the processed optical signals to an operation part 210.

Signals from the first optical detector 121 and the second optical detector 122 may enter Analog-to-Digital Converters (ADCs) 131 and 132 belonging to the ECM 130, and then may pass a Data Transfer Module (DTM) 133 to enter the operation part 210 of the main body via a bidirectional bus. Here, the DTM 133 may serve to select data as a multiplexer that performs time-sharing control transmission. The synchronization function of the DTM 133 and the relay switch may be performed by a command from the main body through the bidirectional bus.

The main body 200 may be configured to control a driver module 134 corresponding to the light source switching control unit and control a loading module of the reference sample R into a measurement insertion part. Also, the main body may perform statistical processing of signals and calculate corrected fluorescence values according to the equations described above. The main body may perform works related to signal processing & control and data input, and may be configured to output the work results via the display part 220.

In an exemplary embodiment of the present invention, in order to detect the skin fluorescence with respect to AGE, light with the first wavelength of 370 nm±20 nm may be used as excitation light for fluorescence excitation, and light with the second wavelength of 440 nm±20 nm corresponding to the wavelength of the skin fluorescence with respect to AGE may be used as the emission light.

In this case, the first light source 111 may include a light emitting diode that irradiates light of the first wavelength range, 370 nm±20 nm. The second light source 112 may include a light emitting diode that irradiates light of the second wavelength range, 440 nm±20 nm. Also, the first optical detector 121 may include a photodiode that detects light of the first wavelength range, and the second optical detector 122 may include a photodiode that detects light of the second wavelength range.

FIG. 3 is a view illustrating a transmitted light detection type measurement apparatus for skin fluorescence according to another exemplary embodiment of the present invention. In FIG. 3, a pair of light guides may be separately disposed at the side of light sources and optical detectors, respectively.

As shown in FIG. 2, the transmitted light detection type measurement apparatus for skin fluorescence may also include a first light source, a second light source, a first optical detector, a second optical detector, and an electronic control module. Unlike in FIG. 2, however, individual light guides, not common light guides, may be connected to the light sources and the optical detectors to transmit light.

Accordingly, in FIG. 3, a first light source light guide 314 and a second light source light guide 315 may be connected to a first light source 311 and a second light source 312, respectively. At the opposite side, a first detection light guide 325 and a second detection light guide 326 may be connected to a first optical detector 321 and a second optical detector 322, respectively.

In this embodiment, since light transmission for light irradiation and light detection may be performed through the respective light guides 314, 315, 325 and 326, a dichroic mirror may not be needed to gather or diffuse light like in FIG. 2.

Also, since light is transmitted through the light guides directly connected to the light sources and the optical detectors without passing an optical system such as a dichroic mirror, objective lenses may not be needed to condense light.

Like in FIG. 2 described above, the main body 400 may include a light source filter 313, first and second detection filters 323 and 324, analog-to-digital converters 331 and 332, a data transfer module 333, an operation part 410 connected to the data transfer module 333, and a display part 420.

FIG. 4 is a view illustrating a transmitted light detection type measurement apparatus for skin fluorescence according to still another exemplary embodiment of the present invention. In FIG. 4, light sources and optical detectors may be disposed at the distal end of the optical sensor, and may directly perform light irradiation and light detection on a measurement target.

In this embodiment, a first light source 511 and a second light source 512 may be disposed on the same chip, and may generate light of a first wavelength λ1 and a second wavelength λ2, respectively. In this case, when light from the first light source 511 does not include a spectrum component of the second wavelength λ2, filters may not be needed.

The optical detector may be divided into two sectors, including a first optical detector 521 and a second optical detector 522, and band-pass filters may be disposed at the front of the two sectors to divide light into the first wavelength λ1 and the second wavelength λ2. An electronic control module may serve to sequentially turn on/off the first light source 511 and the second light source 512, and may control and synchronize optical detection signals received via two channels using a time-sharing method.

In this embodiment, as the light sources 511 and 512 and the optical detectors 521 and 522 are located to face each other, the end portion of the light sources 511 and 512 and the end portion of the optical detectors 521 and 522 may form a clip form, allowing the measurement target to be fixed while pressing the measurement target. In this case, the measurement target may be fitted into a clip form of optical sensor, and then light irradiation and light detection processes may be performed on the measurement target. Thereafter, when the measurement is removed, and a reference sample is fitted into the clip, the light irradiation and light detection processes that have been performed on the measurement target may be automatically performed on the reference sample.

Thereafter, after conversion into a corresponding digital signal, data about measured optical signals may be transmitted to a main body 600 fixed through a communication module, and an operation part 610 may calculate corrected skin fluorescence values regarding the actual measurement target using data about the transmitted fluorescence signals and transmitted light signals. The calculation results may be displayed via a display part 520 on the main body 600 to the outside.

Meanwhile, an optical transmitter such as an optical prism or an optical pipe may be provided to improve the optical transmission and detection efficiencies.

The optical transmitter including the optical prism or the optical pipe may serve to intensively irradiate uniform light on a narrow region of a skin part to be measured, and may concentrate transmitted light on the optical detector.

The optical transmitter included in the optical sensor according to the embodiment of the present invention may have a structure in which light that is not irradiated on the region to be measured is also transmitted to the measurement region or the optical detector without a loss. Accordingly, the optical transmitter may have a mounting surface mounted with a light source or an optical detector and at least one reflection surface in addition to the mounting surface to enable the internal reflection of incident light. Also, the optical transmitter may include a contact surface that contacts a measurement target in addition to the mounting surface and the reflection surface.

Thus, the optical transmitter including the mounting surface, the reflection surface, and the contact surface may be implemented in an optical prism or an optical pipe described in detail below. An exemplary optical sensor including the optical transmitter is illustrated in detail in FIGS. 5 through 8.

Figure 5:
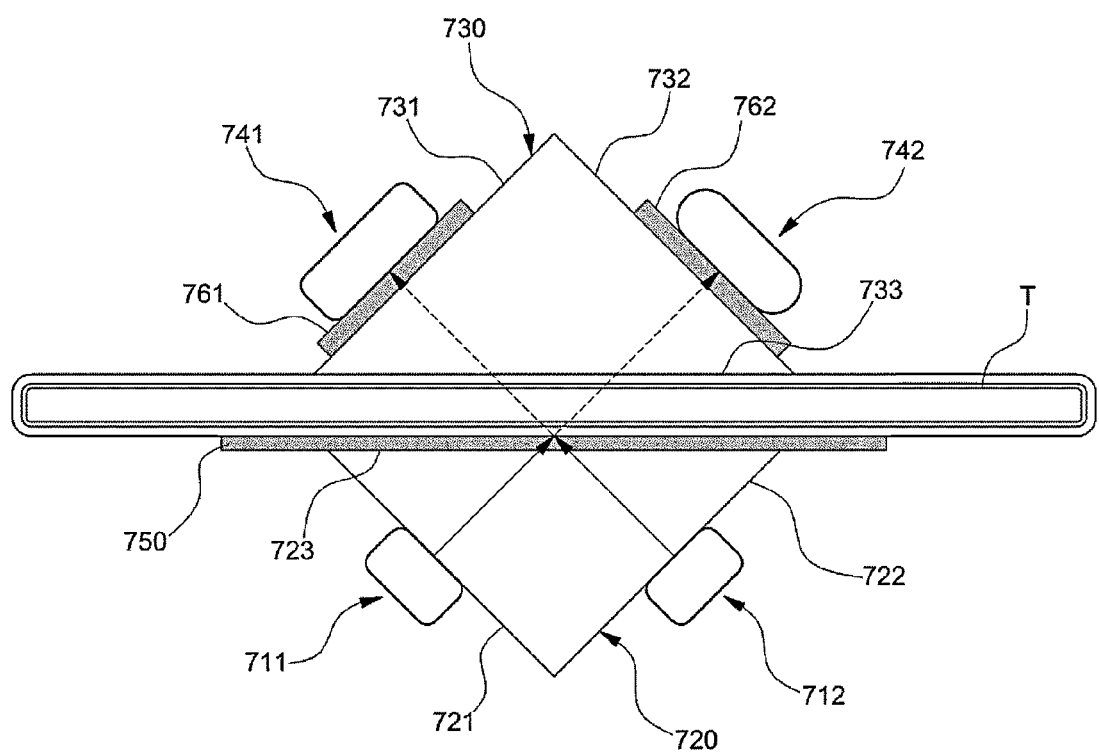
FIG. 5 is a view illustrating a transmitted light detection type measurement apparatus for skin fluorescence according to an embodiment of the present invention in which an optical prism is used.

FIG. 5 illustrates an exemplary transmitted light detection type measurement apparatus for skin fluorescence according to an embodiment of the present invention, in which an optical prism is used.

Since Light Emitting Diode (LED) light sources widely used as an excitation light source irradiates light with a wide divergence, an optical loss may occur on a measurement target, and scattering of fluorescence from the skin on which light is irradiated may cause a loss of the quantity of light detected by the optical detector 320.

Since the skin fluorescence detected is significantly smaller than other excitation light or reflected light thereof, the optical loss may considerably reduce the accuracy of the measurement and the reliability of the diagnosis even when the optical loss is slight.

On the other hand, in order to prevent the optical loss, a transmitted light detection type measurement apparatus for skin fluorescence including optical prism 720 and 730 as an optical transmitter is proposed as shown in FIG. 5.

In this embodiment, excitation light irradiated from the light source may be concentrated by the optical prism, and the optical uniformity of a skin part that is the measurement target can be improved. Also, transmitted light and fluorescence that transmit the measurement target may be transmitted to an optical detector through another optical prism.

Referring to FIG. 5, the transmitted light detection type measurement apparatus for skin fluorescence may include the optical prism 720 at the side of the light source and the optical prism 730 at the side of the optical detector, respectively. In order to discriminate between the two optical prisms 720 and 730, the optical prism adjacent to the light sources 711 and 712 will be referred to as a first optical prism 720, and the optical prism adjacent to the optical detectors 741 and 742 will be referred to as a second optical prism 730.

The first optical prism 720 may include a mounting surface in which light sources are mounted and a reflection surface for reflecting a portion of light that is not transmitted to the measurement target among light incident through the mounting surface.

In FIG. 5, based on the first light source 711, the optical prism surface on which the first light source 711 is disposed may be a mounting surface 721, and the optical prism surface that is adjacent to the mounting surface 721 and can reflect light irradiated from the first light source 711 may be a reflection surface 722.

On the other hand, based on the second light source 712, the optical prism surface that is the reflection surface 722 with respect to the first light source 711 may become a mounting surface 722 of the second light source, and the mounting surface 721 with respect to the first light source 711 may become a reflection surface 722.

In this embodiment including a plurality of light sources, the mounting surface and the reflection surface may be a relative concept that is determined based on any one of light sources. The transmitted light detection type measurement apparatus for skin fluorescence has only to include the mounting surface and the reflection surface based on a specific light source. Accordingly, light irradiated from the light source may be totally reflected from the inside to be maximally concentrated on the skin, thereby reducing the non-uniformity of the light source, i.e., the characteristics in which the optical intensity becomes smaller at the outer side of the optical axis than at the center of the optical axis and thus achieving improved optical uniformity In this case, a filter may be disposed on the mounting surface (or reflection surface) of the optical prism to transmit only a specific wavelength of light.

Also, in addition to the mounting surface and the reflection surface, the first optical prism 720 may further include a contact surface 723 at the side of the first optical prism 720. The contact surface 723 may contact or get close to the measurement target T and press the measurement part during the measurement. The contact surface 723 may be a surface of the first optical prism 720 that is connected to the measurement part. Light may be transmitted to the measurement part through the contact surface 723.

Meanwhile, light that passes through the contact surface 723 of the first optical prism 720 may generate fluorescence inside the skin, and then may be emitted to the optical detectors 741 and 742 together with transmitted light. Accordingly, as shown in FIG. 5, in an exemplary embodiment, a second optical prism 730 may be further disposed as another optical transmitter for efficiently transmitting the transmitted light and the fluorescence that are transmitted to the optical detectors 741 and 742.

Similarly to the first optical prism 720, the second optical prism, based on the first optical detector 741, may be configured to include a mounting surface 731 mounted with an optical detector, a reflection surface 732 that is an optical prism surface that is adjacent to the mounting surface and reflects transmitted light and fluorescence, and a contact surface 733 that contacts or gets close to the measurement part and presses the measurement part.

The second optical prism 730 may be configured to allow the transmitted light and the fluorescence that pass through the skin that is the measurement target to enter the optical detector directly or the optical detectors 741 and 742 through the internal reflection.

Meanwhile, the transmitted light detection type measurement apparatus for skin fluorescence according to the embodiment of the present invention may be configured to include an optical connector 750 for preventing a light leakage that may occur between two media due to the optical diffraction and scattering of the transmitted light and the fluorescence from the skin part that is the measurement target T at a contact surface between the optical prism 720 and the skin part.

The optical connector 750 may be configured to locate between the contact surface of the optical prism adjacent to the skin that is the measurement target and the surface of the skin, and may contact the contact surface of the optical prism and the surface of the skin, respectively.

The optical connector 340 may be disposed over the contact surface of the first optical prism 720, and may contact the contact surface and the surface of the skin to serve as a connection layer for allowing a smooth optical contact with an appropriate refractive index at the boundaries thereof.

The optical connector 750 may control a certain refractive index between the two media to prevent a light leakage that may occur between the two media due to the refraction and scattering of the excitation light between the optical prism and the skin tissue, and may serve to fill uneven portions such as fine unevenness of the skin tissue.

The optical connector 750 may be formed of an elastic material or a liquid material such as water or oil-immersion. The optical connector 750 may be formed of a material having a refractive index similar to those of the optical prism and the skin.

Due to the optical connector 750, the total internal reflection of the irradiated light may not occur at the boundaries between the prism and the skin tissue, and the transmission efficiency of light emitting from the light source into the skin can be significantly improved.

Accordingly, the transmitted light detection type measurement apparatus for skin fluorescence including the optical prism and the optical connector 750 can improve the optical concentration and the optical uniformity, and can significantly reduce the specular reflection component of the transmitted light and the fluorescence at the contact surface.

Meanwhile, as shown in FIG. 5, the transmitted light detection type measurement apparatus for skin fluorescence may be configured to include a light source switching controller (not shown) for controlling turning on/off of the two light sources 711 and 712 and the two optical detectors 741 and 742 in addition to an operator (not shown) for calculating a corrected skin fluorescence signal from a fluorescence signal and a transmitted light signal detected by the two optical detectors 741 and 742.

In this case, as shown in FIG. 5, the first optical prism 720 and the second optical prism 730 may be configured with triangular prisms that have a contact surface adjacent to the skin and two mounting surfaces (or reflection surfaces).

Also, the mounting surfaces of the optical prisms may be mounted with light sources and optical detectors. For example, as shown in FIG. 5, the two light sources 711 and 712 may be disposed over the two mounting surfaces of the first optical prism 720, and the two optical detectors 741 and 742 may be disposed over the two mounting surfaces of the second optical prism 730. In this case, filters 761 and 762 may be disposed on the mounting surfaces of the second optical prism 730 to remove noise and pass only a certain wavelength range of light The structural features such as the mounting location of the light sources and the optical detectors and the shape of the optical prism can be appropriately modified according to the need. For example, the optical prism may be a trapezoidal prism having a trapezoidal section. The light sources and the optical detectors may be appropriately disposed over the mounting surfaces other than the contact surface.

Also, the transmitted light detection type measurement apparatus for skin fluorescence can obtain a corrected skin fluorescence value through the same operation process as that as described in FIG. 2 except that the optical irradiation and the optical detection are performed through the optical prism.

Figure 6:
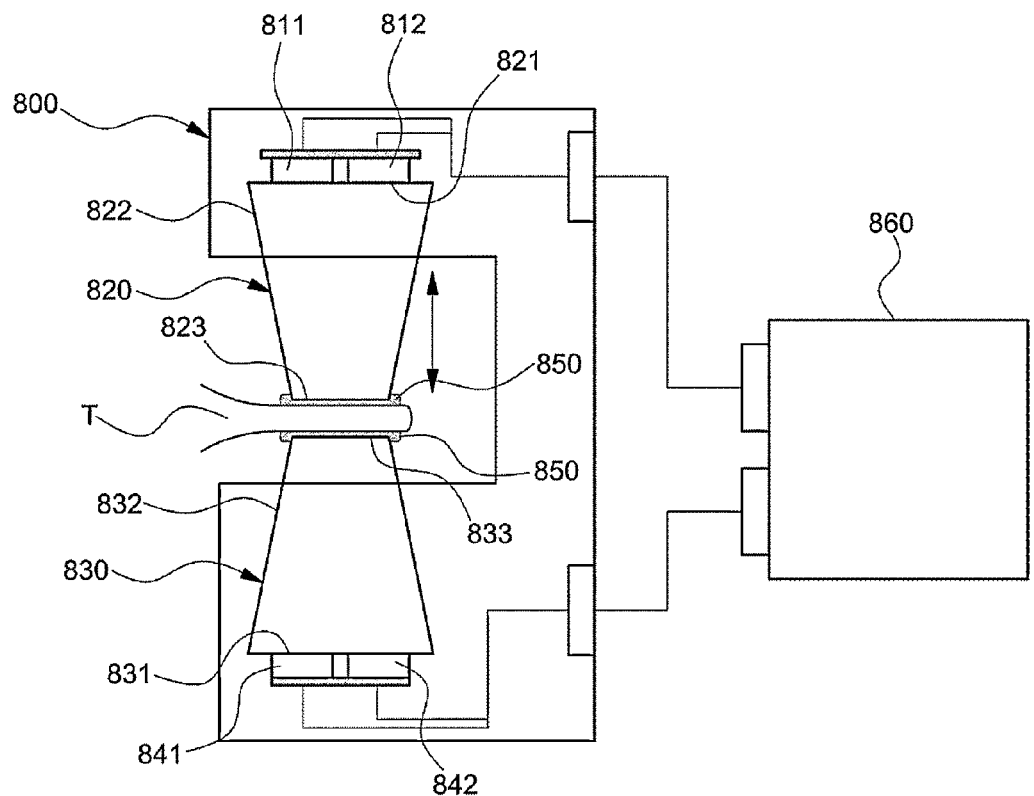
FIGS. 6 through 10 are views illustrating a transmitted light detection type measurement apparatus for skin fluorescence according to another embodiment of the present invention.
Figure 7:
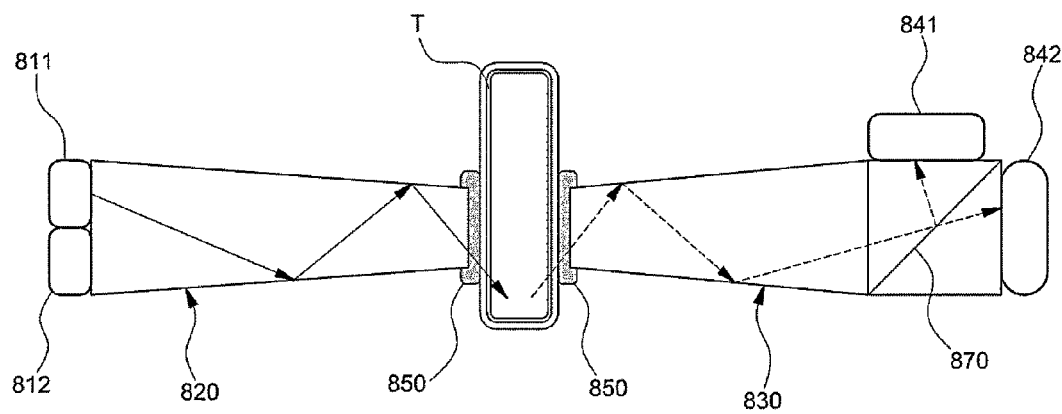

FIGS. 6 and 7 illustrate a transmitted light detection type measurement apparatus for skin fluorescence according to another embodiment of the present invention, where an optical pipe is used as an optical transmitter.

Referring to FIG. 6, two optical pipes 820 and 830 instead of the two optical prisms may be used as the optical transmitter that transmits light from a light source and secondary light such as fluorescence and transmitted light that passes through the skin to the optical detector.

In this embodiment, the optical pipes 820 and 830 may be formed of glass similarly to the optical prism. As shown in FIG. 6, the optical pipes 820 and 830 may be tapered in a polyprism or cylindrical shape. The optical pipes 820 and 830 may have two surfaces at both ends thereof, respectively. The light source or the optical detector may be located at the side of larger one of the two surfaces. The smaller surface may be configured to contact the skin tissue to be measured. Accordingly, the optical pipes may be formed in a tapered pillar shape having an inclined side surface. In this case, the first optical pipe 820 at the side of the light source and the second optical pipe 830 at the side of the optical detector may be symmetrically disposed such that the skin is placed therebetween as shown in FIG. 6.

Accordingly, the optical pipes 820 and 830 may have mounting surfaces 821 and 831 on which the light sources 811 and 812 or the optical detectors 841 and 842 are disposed, reflection surfaces 822 connected to the mounting surfaces 821 and 831 and extending toward the skin tissue, and contact surfaces 823 and 833 connected to the reflection surfaces 822 and 832 and contacting the skin tissue, respectively.

In the transmitted light detection type measurement apparatus for skin fluorescence having the optical pipes, light irradiated from the light source may be reflected along the reflection surfaces 822 and 832 that are inclined, and then may be transmitted to the measurement target T. Thereafter, light may enter the skin tissue through the contact surfaces 823 and 833 of the optical pipes 820 and 830 that contact the skin tissue.

Accordingly, since the optical pipe having a tapered shape in which the cross-sectional area is gradually reduced from the mounting surface to the contact surface is used, light emitting from the light source can be concentrated on a contact region with the skin, increasing the optical concentration of irradiated light.

The optical pipe may allow even light from an LED light source having a relatively wider divergence angle to be concentrated on a narrow region. Also, even when a plurality of light sources having different optical axes are used, light can become uniform, and the optical axes of light irradiated on the skin can be aligned while passing through the optical pipe.

Furthermore, since the optical axes of the light sources and the optical axes of the optical detectors can be aligned, the accuracy of the detection can be improved.

In addition, since light is reflected and transmitted along the reflection surfaces that are inclined, uniform light can be irradiated on a wider range by increasing the Numerical Aperture (NA) at a part contacting the skin, thereby increasing occurrence of secondary light.

The second optical pipe 830 may be disposed at the opposite side of the first optical pipe 820 at the side of the light source. Transmitted light and fluorescence that pass the second pipe 830 may be detected by the optical detector disposed over the mounting surface of the second optical pipe 830. The transmitted light and fluorescence among light transmitted to the skin along the reflection surface 822 of the first optical pipe 820 may be emitted out of the opposite side of the skin, and may be transmitted to the optical detector along the reflection surface 832 of the second optical pipe 830.

Optical signals detected by the optical detector may be transmitted to a main body 860 including an operator. As described above, the main body 860 may calculate a corrected skin fluorescence value regarding an actual measurement target using data about the fluorescence signals and the transmitted light signals that are transmitted.

Figure 12:
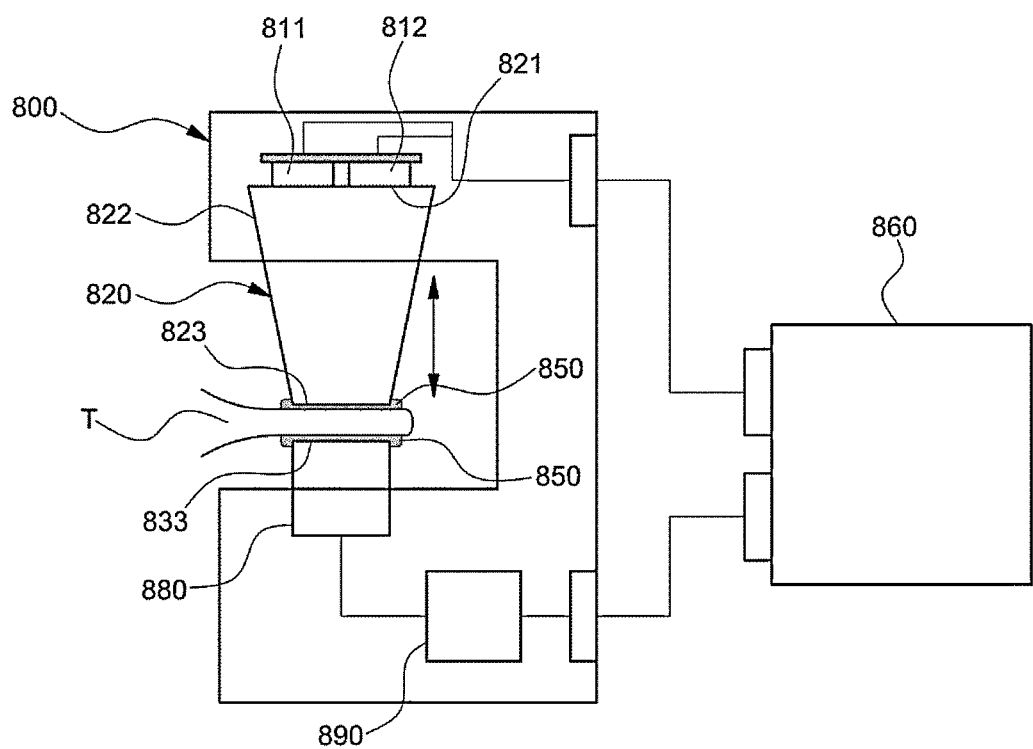
FIG. 12 is a view illustrating a transmitted light detection type measurement apparatus for skin fluorescence according to yet another embodiment of the present invention in which modified optic fibers are used.

In another exemplary embodiment of the present invention, optic fibers may be used instead of optic pipe as shown in FIG. 12. Specifically, the second optical pipe 830 may be replaced with optical fiber or optical fiber bundle 880 and the optical fiber or optical fiber bundle 880 may be configured to be connected to an optical spectrometer 890. In this case, the optical fibers may be disposed at the opposite side of the first optical pipe 820, and an optical spectrometer 890 may be disposed to detect transmitted light and fluorescence that pass through the optical fibers.

FIG. 7 illustrates a modified example of the transmitted light detection type measurement apparatus for skin fluorescence shown in FIG. 6, where a dichroic prism is disposed at the side of the optical detector.

As shown in FIG. 7, a dichroic prism 870 may be disposed between the mounting surface of the second optical pipe 830 and the optical detector. The dichroic prism 870 may divide secondary light occurring in the skin tissue into two wavelength ranges $\lambda_1$ and $\lambda_2$.

Light divided into two wavelength ranges may be detected by the optical detectors 841 and 842. The optical detectors 841 and 842 for each wavelength range may be disposed over different surfaces of the optical pipe. Accordingly, the numerical aperture of light reduced compared to light introduced into the skin tissue can be improved by the two optical detectors 841 and 842 disposed over different surfaces as described above.

As described above, due to the first optical pipe 820 and the second optical pipe 830, a measurement error can be reduced by matching the optical axes in spite of a spatial mismatch between the light source and the optical detector.

Similarly to the previous embodiment including the optical prism, an optical connector 850 may be disposed between the skin part that is the measurement target and the contact surface of the first optical pipe 820. The optical connector 850 may be disposed at the first optical pipe 820 and the second optical pipe 830, and a detailed description of the optical connector 850 will be omitted herein.

Figure 8:
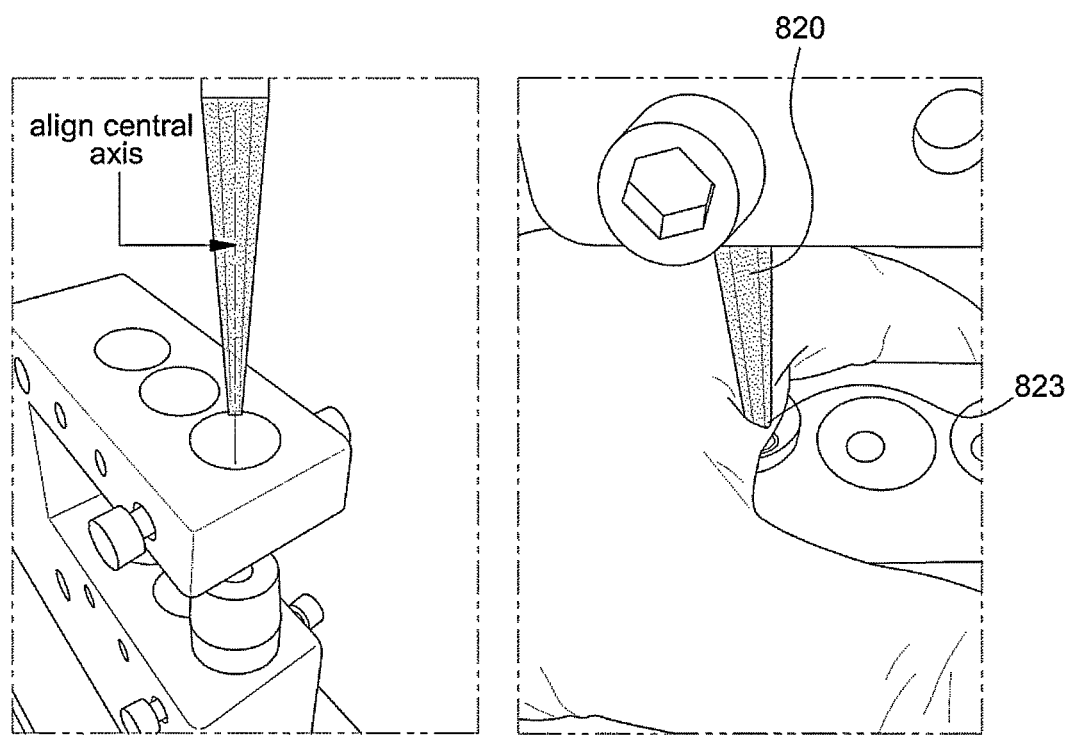
Figure 9:
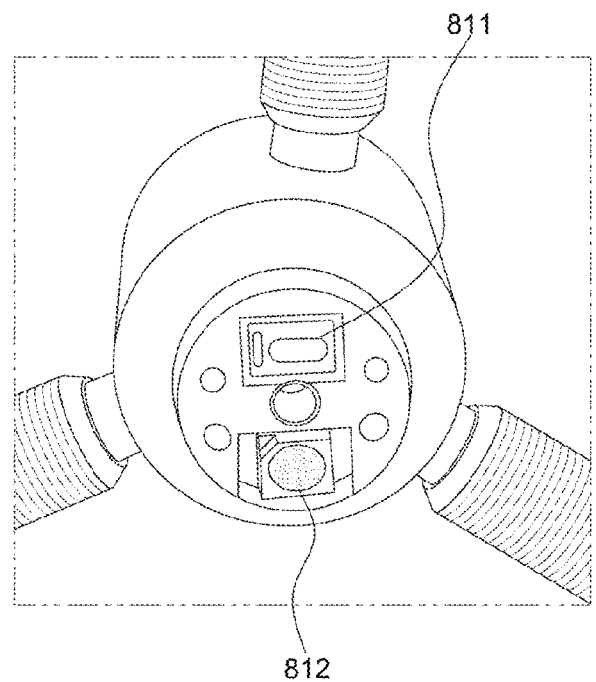
Figure 10:
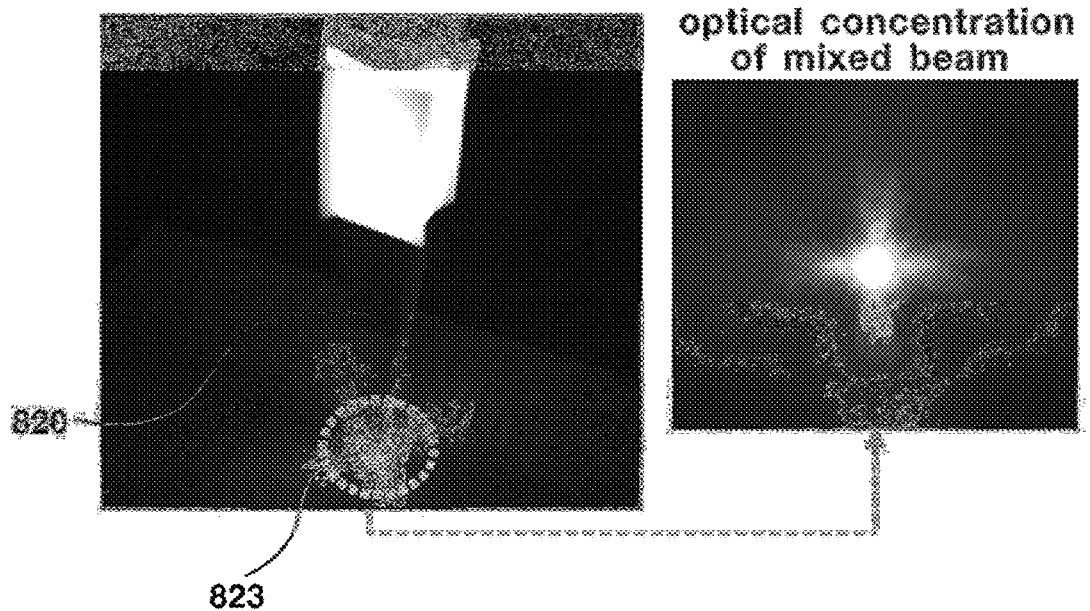

FIGS. 8 through 10 illustrate an actual example of the transmitted light detection type measurement apparatus for skin fluorescence manufactured as shown in FIG. 6, which shows an optical sensor as a main component. The optical sensor may include a light source, an optical detector, and two optical pipes. The optical sensor may include a transfer part for transferring the optical pipe in a vertical direction for pressing the measurement target T and a thickness indicator for indicating the thickness of the skin varying according to the rising and falling of the optical pipe by the transfer part. Also, the optical sensor may be configured to be connected to the main body for controlling the light source and the optical sensor and collecting the measurement data.

As shown in FIG. 8, a space may be provided between the first optical pipe 820 and the second optical pipe 830 to insert the measurement target T. As shown in FIG. 8, the light source may include two light sources 811 and 812 for emitting light of different wavelength ranges.

A specific measurement process using the transmitted light detection type measurement apparatus for skin fluorescence configured as above will be described below.

An optical sensor 800 may be placed at a skin part between the thumb and the index finger, and then the first optical pipe 820 may be lowered to allow the light source to irradiate light.

In this case, a mixed light may be irradiated from two light sources through the first optical pipe 820 as shown in FIG. 10. Particularly, the distribution characteristics of the mixed light can be seen from the right magnified view. In the optical distribution characteristics, it can be seen that the mixed light has a uniform distribution and is concentrated on the measurement target T.

Light concentrated on a region to be measured may be divided into transmitted light that passes through the skin and skin fluorescence generated by fluorescence excitation, which are detected by the optical detector through the second optical pipe 830.

In this case, in order to improve the reliability of the measurement, a process of maintaining the thickness of the skin part to be measured may be performed. For this, a transfer part (not shown) may be provided to press the skin part that is the measurement target T by transferring the first optical pipe. Also, a thickness indicator (not shown) may be provided to measure the thickness of the skin while the skin part is being pressed by the first and second pipes transferred by the transfer part.

Accordingly, during the measurement process, the transfer part may transfer the first optical pipe 820 to press the skin part, and then the thickness indicator may measure a distance between the first optical pipe 820 and the second optical pipe 830 to check the thickness of the measurement target. When the skin part is pressed to a predetermined thickness, the transfer may be stopped.

Due to the above process, the thickness of the measurement target can be fixedly maintained, and a certain level of reproducibility can be achieved.

Figure 11:
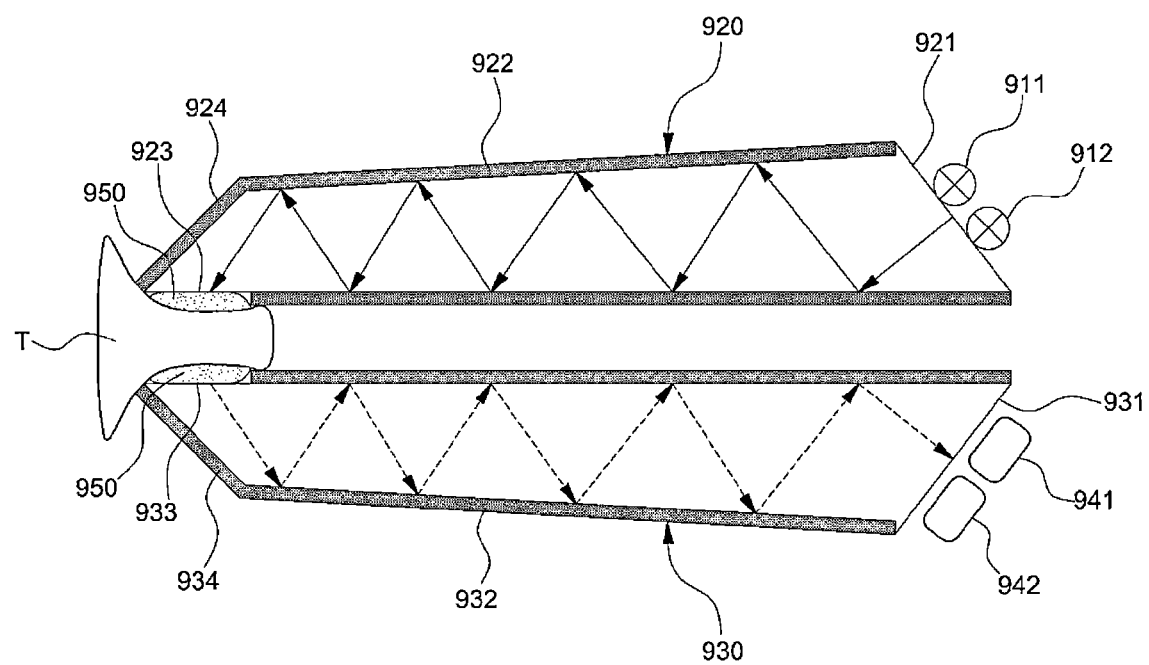
FIG. 11 is a view illustrating a transmitted light detection type measurement apparatus for skin fluorescence according to still another embodiment of the present invention in which a modified optical pipe is used.

FIG. 11 illustrates a modified optical pipe according to another embodiment of the present invention.

FIG. 6 illustrates a vertical-type optical pipe that extends in a perpendicular direction to the contact surface with the measurement target, whereas FIG. 11 illustrates a horizontal-type optical pipe that extends in a substantially parallel direction to the measurement target.

Specifically, the apparatus of FIG. 11 may include light sources, optical detectors, and a horizontal-type optical pipe serving as an optical transmitter for transmitting light from the light source to the optical detector. The horizontal-type optical pipe may include a first optical pipe 920 and a second optical pipe 930 that contact the measurement target T in downward and upward directions, respectively. The optical pipes 920 and 930 may have mounting surfaces 921 and 931 mounted with light sources 911 and 912 or optical detectors 941 and 942, reflection surfaces 922 and 932 for reflecting light irradiated from the light source or transmitted light and fluorescence that pass through the skin, and contact surfaces 923 and 933 contacting the measurement target T, respectively.

In this embodiment, the first optical pipe 920 may be disposed such that the mounting surface 921 of the light source is inclined to the reflection surface 922 to effectively allow uniform light to be incident to the contact surface 923 with the measurement target T substantially parallel to the reflection surface 922. Accordingly, irradiation light from the light source disposed over the mounting surface 921 may be reflected along the reflection surface 922, and may enter the measurement target T through the contact surface 923. Similarly, the mounting surface 931 at the side of the optical detector may also be disposed inclined to the reflection surface 932 of the second optical pipe 930.

Also, as shown in FIG. 11, the first optical pipe 920 and the second optical pipe 930 may have bent reflection surfaces 924 and 934 inclined to the contact surfaces 923 and 933 to allow the irradiation light to be effectively incident to the measurement target T and allow the transmitted light and the fluorescence to be effectively incident to the optical detectors 941 and 942.

In this embodiment, mirror coating may be performed on the reflection surface through a separate deposition process such that light reflection occurs on the reflection surface of the optical pipe. The mirror coating may not be performed on the contact surface of the optical pipe such that light can be transmitted to the skin. Accordingly, light irradiation and collection of secondary light may be performed through the contact surface without mirror coating. Also, the mirror coating may not be performed on the mounting surface over which the light source and the optical detector are located.

Similarly to the previous embodiments, an optical connector 950 may be inserted between the contact surfaces 923 and 933 of the optical pipe and the measurement target T. The optical connector 950 can improve the optical transmission efficiency. Also, a transfer part and a thickness indicator for pressing the measurement target and maintaining the thickness thereof may be provided similarly to those of FIG. 6.

Accordingly, in the embodiment using the horizontal-type optical pipe as shown in FIG. 11, since the optical sensor can be simply configured in a clip type, the measurement can be easily performed.

As described above, a transmitted light detection type measurement apparatus for skin fluorescence according to an embodiment of the present invention has the following advantages.

First, since diabetic diseases can be easily diagnosed by evaluating the skin autofluorescence, mass inspection can be performed to find potential diabetic patients. Also, the risk of cardiac-vascular diseases and complications thereof can be predicted.

Second, since the optical concentration and the optical uniformity of light irradiated from a light source are improved, more uniform light can be irradiated on the measurement target.

Third, since the optical efficiency can be improved by efficiently concentrating light from a light source on the skin tissue and minimizing the specular reflection on the surface of the skin tissue, the miniaturization of the apparatus can be achieved.

Fourth, in measuring skin fluorescence, it is possible to fundamentally remove an error occurrence factor due to specular reflection from skin surface by a transmitted light measuring method, and influences of the external factors such as roughness of the skin, scar, and hair and the internal factors such as pigments and hemoglobin of blood can be minimized, thereby exactly diagnosing diseases Fifth, since an error due to light scattering and absorption generated inside the skin can be simply corrected, exact measurement of the skin fluorescence and exact diagnosis of diseases using the skin fluorescence can be achieved.

Sixth, the transmitted light detection type measurement apparatus for skin fluorescence may include light sources and optical detectors, and may be manufactured in a form of hand-grippable small-size scanner to measure the skin fluorescence. Thus, since a user can scan a diagnostic target by contacting the scanner with the skin of a subject, non-invasive diagnosis can be performed in real-time.

The invention has been described in detail with reference to exemplary embodiments thereof. However, it will be appreciated by those skilled in the art that changes may be made in these embodiments without departing from the principles and spirit of the invention, the scope of which is defined in the appended claims and their equivalents.

What is claimed is:

1. A transmitted light type measurement apparatus measuring skin fluorescence, which is configured to perform light irradiation and light detection on a reference sample or a measurement target, the apparatus comprising:
    a first light source configured to irradiate excitation light on the measurement target;
    a second light source configured to irradiate light, which has a same wavelength range as light generated from the measurement target by the excitation light from the first light source;
    a first optical detector disposed to detect transmitted light through the measurement target by the excitation light from the first light source;
    a second optical detector disposed to detect the skin fluorescence generated from the measurement target by the excitation light from the first light source and transmitted light passing through the measurement target by light from the second light source;
    a light source switching controller configured to control turning on and off of the first light source and the second light source; and
    an operation part configured to calculate a skin fluorescence signal by correcting a signal based on the skin fluorescence and the transmitted light detected by the first optical detector and the second optical detector,
    wherein the operation part calculates a skin fluorescence value corrected by an equation:

$AFcorr = K[I(\lambda 2, t1)/I_0(\lambda 2, t1)]/\{[T(\lambda 1)]^{k1}[T(\lambda 2)]\}^{k2}$ (here, $T(\lambda 1) = I(\lambda 1, t1)/I_0(\lambda 1, t1)$:

Diffuse transmission coefficient in excitation wavelength;

$T(\lambda 2) = I(\lambda 2, t2)/I0(\lambda 2, t2)$:

Diffuse transmission coefficient in emission wavelength;
    $I(\lambda 2, t1)$: Inherent fluorescence signal value of skin tissue;
    $I(\lambda 1, t1)$: Transmitted light signal value of skin tissue in excitation light wavelength;
    $I(\lambda 2, t2)$: Transmitted light signal value of skin tissue in emission light wavelength;
    k1, k2: Exponents of correction function with respect to excitation light and emission light wavelength;
    $I0(\lambda 2, t1)$: Inherent fluorescence signal value of reference sample;
    $I0(\lambda 1, t1)$: Transmitted light signal value of reference sample in excitation light wavelength;
    $I0(\lambda 2, t2)$: Transmitted light signal value of reference sample in emission light wavelength); and
    K: Ratio coefficient that considers the features of the used reference samples).

2. The transmitted light detection type measurement apparatus of claim 1, further comprising:
    a pair of optical transmitters configured to transmit the excitation light irradiated from the first light source and the second light source to the measurement target, transmit the transmitted light to the first optical detector and the second optical detector and transmit the skin fluorescence signal to the second optical detector;
    wherein the optical transmitters have a mounting surface mounted with the first light source and the second light source or the first optical detector and the second light source, a reflection surface extending from the mounting surface to the measurement target and reflecting light, and a contact surface connected such that light is incident to the measurement target.

3. The transmitted light detection type measurement apparatus of claim 2, wherein the pair of optical transmitters comprise a first optical prism connected to the first light source and the second light source and a second optical prism connected to the first optical detector and the second optical detector.

4. The transmitted light detection type measurement apparatus of claim 3, wherein the first optical prism and the second optical prism are triangular prisms having a triangular section.

5. The transmitted light detection type measurement apparatus of claim 4, wherein the first optical prism has a mounting surface mounted with the first light source and a reflection surface mounted with the second light source.

6. The transmitted light detection type measurement apparatus of claim 5, wherein the second optical prism has a mounting surface mounted with the first optical detector and a reflection surface mounted with the second optical detector.

7. The transmitted light detection type measurement apparatus of claim 2, wherein the pair of optical transmitters comprise a first optical pipe connected to the first light source and the second light source and a second optical pipe connected to the first optical detector and the second optical detector.

8. The transmitted light detection type measurement apparatus of claim 7, wherein the first optical pipe and the second optical pipe have reflection surfaces that are inclined, and have a tapered pillar shape in which a mounting surface is wider than a contact surface.

9. The transmitted light detection type measurement apparatus of claim 8, wherein the reflection surfaces of the first optical pipe and the second optical pipe are tapered such that a cross-sectional area thereof is reduced from the mounting surface to the contact surface.

10. The transmitted light detection type measurement apparatus of claim 7, wherein the first optical pipe has a mounting surface mounted with the first light source and the second light source.

11. The transmitted light detection type measurement apparatus of claim 10, wherein the mounting surfaces of the first optical pipe and the second optical pipe are inclined to the reflection surface thereof.

12. The transmitted light detection type measurement apparatus of claim 7, wherein the second optical pipe has a mounting surface mounted with the first optical detector and the second optical detector.

13. The transmitted light detection type measurement apparatus of claim 7, further comprising a dichroic prism at a side of the mounting surface of the second optical pipe for dividing detected light into two wavelength bands.

14. The transmitted light detection type measurement apparatus of claim 13, where the first optical detector is disposed to detect reflected light from the dichroic prism, and the second optical detector is disposed to detect transmitted light from the dichroic prism.

15. The transmitted light detection type measurement apparatus of claim 7, wherein the first optical pipe and the second optical pipe are vertical-type optical pipes that extend in a perpendicular direction to the contact surface with the measurement target.

16. The transmitted light detection type measurement apparatus of claim 7, wherein the first optical pipe and the second optical pipe are horizontal-type optical pipes that extend in a parallel direction to the contact surface with the measurement target.

17. The transmitted light detection type measurement apparatus of claim 16, wherein the reflection surfaces of the first optical pipe and the second optical pipe comprise a bent reflection surface that is inclined to the contact surface, respectively.

18. The transmitted light detection type measurement apparatus of claim 16, wherein the reflection surfaces of the first optical pipe and the second optical pipe are processed by mirror coating.

19. The transmitted light detection type measurement apparatus of claim 2, further comprising: a transfer part configured to move the optical transmitter in a vertical direction; and a thickness indicator configured to measure a distance between the two optical transmitters and indicating a thickness of the measurement target.

20. The transmitted light detection type measurement apparatus of claim 2, further comprising an optical connector disposed over the contact surface of the optical transmitter and contacting the measurement target.

21. The transmitted light detection type measurement apparatus of claim 20, wherein the optical connector serves as a connection layer formed of a liquid material or an elastic material between the optical transmitter and the measurement target.

22. The transmitted light detection type measurement apparatus of claim 1, wherein the light source switching controller is further configured to control the first light source and the second light source such that turning-on states of the first light source and the second light source are separated from each other in time.

23. The transmitted light detection type measurement apparatus of claim 22, wherein the switching controller is further configured to detect the skin fluorescence signal and the transmitted light signal from the first light source and the transmitted light signal from the second light source while continuously repeating a process of sequentially turning on and off the first light source and the second light source.

24. The transmitted light detection type measurement apparatus of claim 1, wherein the measurement target and the reference sample are selectively located on optical paths of the first light source and the second light source.

25. The transmitted light detection type measurement apparatus of claim 1, wherein the first light source irradiates light with a wavelength of 370±20 nm.

26. The transmitted light detection type measurement apparatus of claim 1, wherein the second light source irradiates light with a wavelength of 440±20 nm.

27. The transmitted light detection type measurement apparatus of claim 1, wherein the switching controller is further configured to control all the first light source and the second light source to be turned off before turning on each of the light sources.

28. The transmitted light detection type measurement apparatus of claim 27, wherein when the switching controller turns off all the first light source and the second light source, the first optical detector and the second optical detector measure dark signals, and the operation part stores the measured dark signals and compensate for the skin fluorescence signal and the transmitted light signal detected from the stored dark signals.

29. The transmitted light detection type measurement apparatus of claim 1, wherein the switching controller is further configured to control the first light source and the second light source to repeat turning on and off at a period of about 10 Hz to about 100 Hz.

30. The transmitted light detection type measurement apparatus of claim 1, further comprising an optical detector switching controller for controlling turning on and off of the first optical detector and the second optical detector.

31. The transmitted light detection type measurement apparatus of claim 1, comprising: an optical sensor comprising the first light source, the second light source, the first optical detector, and the second optical detector; and a main body electrically connected to the optical sensor and comprising the operation part, wherein the optical sensor is detachable from the main body.

32. The transmitted light detection type measurement apparatus of claim 31, wherein the optical sensor comprises a memory for storing detected data.

33. The transmitted light detection type measurement apparatus of claim 1, comprising: an optical sensor comprising the first light source, the second light source, the first optical detector, and the second optical detector; and a main body electrically connected to the optical sensor and comprising the operation part, wherein the optical sensor is detachable from the main body; wherein the optical sensor comprises a first fixing part connected to the first light source and the second light source and a second fixing part connected to the first optical detector and the second optical detector, and the first and second fixing parts face each other to form an insertion space therebetween.

34. The transmitted light detection type measurement apparatus of claim 33, wherein the first light source and the second light source are disposed at a distal end of the first fixing part to directly irradiate light on the measurement target, and the first optical detector and the second detector are disposed at a distal end of the second fixing part to directly detect the transmitted light and the skin fluorescence.

35. The transmitted light detection type measurement apparatus of claim 34, wherein the first optical detector and the second optical detector are configured to form two sectors, and comprise band-pass filters at the front of the two sectors to divide light into a first wavelength ($\lambda 1$) and a second wavelength ($\lambda 2$), respectively.

36. The transmitted light detection type measurement apparatus of claim 34, wherein the first fixing part and the second fixing part are manufactured in a form of a clip to fix the measurement target while compressing the measurement target.

37. The transmitted light detection type measurement apparatus of claim 33, wherein the reference sample is movably mounted in the optical sensor, and is loaded into the insertion space after the measurement target is removed from the insertion space between the first fixing part and the second fixing part.

38. The transmitted light detection type measurement apparatus of claim 37, wherein the optical sensor performs measurement on a skin when the skin that is the measurement target is located at the insertion space, and performs measurement on the reference sample when the measurement target is removed and then the reference sample is located at the insertion space.

39. The transmitted light detection type measurement apparatus of claim 38, wherein the optical sensor stores measured results about the skin that is the measurement target and the reference sample, and transmits stored data about the skin and reference sample to the main body to allow the operation part to calculate the corrected skin fluorescence signals.

40. The transmitted light detection type measurement apparatus of claim 1, comprising: an optical sensor comprising the first light source, the second light source, the first optical detector, and the second optical detector; and a main body electrically connected to the optical sensor and comprising the operation part, wherein the optical sensor is detachable from the main body; wherein the optical sensor comprises a common light source light guide for transmitting light irradiated from the first light source and the second light source in a shared manner.

41. The transmitted light detection type measurement apparatus of claim 40, wherein the optical sensor comprises a common detection light guide for transmitting the transmitted light and the skin fluorescence to the first optical detector and the second optical detector in a shared manner.

42. The transmitted light detection type measurement apparatus of claim 40, wherein the optical sensor comprises a first dichroic mirror on an optical path to transmit light irradiated from the first light source and the second light source to the common light source light guide.

43. The transmitted light detection type measurement apparatus of claim 42, wherein the optical sensor comprises a second dichroic mirror on an optical path to divide light from the common detection light guide and transmit the divided light to the first optical detector and the second optical detector.

44. The transmitted light detection type measurement apparatus of claim 43, further comprising a first detection filter between the second dichroic mirror and the first optical detector and a second detection filter between the second dichroic mirror and the second optical detector, wherein the first detection filter passes light of a first wavelength and inhibits light of a second wavelength, and the second detection filter inhibits light of the first wavelength and passes light of the second wavelength.

45. The transmitted light detection type measurement apparatus of claim 43, further comprising objective lenses between the first and second optical detectors and the second dichroic mirror to concentrate light passing the second dichroic mirror on the first optical detector and the second optical detector, respectively.

46. The transmitted light detection type measurement apparatus of claim 42, further comprising a light source filter between the first light source and the first dichroic mirror to pass light of a first wavelength irradiated from the first light source and inhibit light of a second wavelength irradiated from the second light source.

47. The transmitted light detection type measurement apparatus of claim 42, further comprising objective lenses between the first and second light sources and the first dichroic mirror to condense light irradiated from the first and second light sources, respectively.

48. The transmitted light detection type measurement apparatus of claim 1, comprising: an optical sensor comprising the first light source, the second light source, the first optical detector, and the second optical detector; a main body electrically connected to the optical sensor and comprising the operation part, wherein the optical sensor is detachable from the main body; and a first light source light guide for transmitting light irradiated from the first light source and a second light source light guide for transmitting light irradiated from the second light source.

49. The transmitted light detection type measurement apparatus of claim 48, wherein the optical sensor comprises a first detection light guide for transmitting the transmitted light of the first light source to the first optical detector and a second detection light guide for transmitting the transmitted light of the second light source or the skin fluorescence to the second optical detector.

50. The transmitted light detection type measurement apparatus of claim 49, further comprising a first detection filter between the first light source light guide and the first optical detector to pass light of a first wavelength and inhibit light of a second wavelength, and a second detection filter between the second light source light guide and the second optical detector to inhibit light of the first wavelength and pass light of the second wavelength.

51. The transmitted light detection type measurement apparatus of claim 48, further comprising an light source filter between the first light source and the first light source light guide to pass light of a first wavelength irradiated from the first light source and inhibit light of a second wavelength irradiated from the second light source.

52. The transmitted light detection type measurement apparatus of claim 1, wherein the main body further comprises a display part, and the display part outputs the corrected skin fluorescence signals calculated in the operation part.

* * * * *